United States Patent
Federspiel et al.

(10) Patent No.: US 11,298,452 B2
(45) Date of Patent: Apr. 12, 2022

(54) EXTRACORPOREAL AMBULATOR ASSIST LUNG

(71) Applicants: University of Pittsburgh—Of the Commonwealth System of Higher Education, Pittsburgh, PA (US); CARNEGIE MELLON UNIVERSITY, Pittsburgh, PA (US)

(72) Inventors: William J. Federspiel, Pittsburgh, PA (US); Brian Joseph Frankowski, Imperial, PA (US); James F. Antaki, Allison Park, PA (US); Christian Andres Bermudez, Philadelphia, PA (US); Richard Garrett Jeffries, Philadelphia, PA (US); William R. Wagner, Gibsonia, PA (US); Sang-Ho Ye, Cheswick, PA (US)

(73) Assignees: University of Pittsburgh—Of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 719 days.

(21) Appl. No.: 16/139,015

(22) Filed: Sep. 22, 2018

(65) Prior Publication Data

US 2019/0022300 A1 Jan. 24, 2019

Related U.S. Application Data

(63) Continuation of application No. 14/647,861, filed as application No. PCT/US2013/072286 on Nov. 27, 2013, now Pat. No. 10,080,834.

(Continued)

(51) Int. Cl.
*A61M 1/36* (2006.01)
*A61M 1/16* (2006.01)
(Continued)

(52) U.S. Cl.
CPC ........ *A61M 1/3667* (2014.02); *A61M 1/1698* (2013.01); *A61M 1/262* (2014.02);
(Continued)

(58) Field of Classification Search
CPC ...... A61M 1/3667; A61M 1/32; A61M 1/262; A61M 1/267; A61M 1/1698;
(Continued)

(56) References Cited

U.S. PATENT DOCUMENTS

| 4,239,729 A | 12/1980 | Hasegawa |
| 5,263,924 A * | 11/1993 | Mathewson ........... B01D 63/02 604/6.14 |

(Continued)

FOREIGN PATENT DOCUMENTS

| EP | 1930034 A1 | 6/2008 |
| EP | 2925382 | 10/2015 |

(Continued)

OTHER PUBLICATIONS

Pacella, HE, et al., Permeability of hollow fiber bundles using in blood oxygenation devices. J of Membrane Sci. 382(1-2): 238-242, 2011.

(Continued)

*Primary Examiner* — Leslie R Deak
(74) *Attorney, Agent, or Firm* — Bartony & Associates, LLC.

(57) ABSTRACT

A extracorporeal system for lung assist includes a housing, a blood flow inlet in fluid connection with the housing; a blood flow outlet in fluid connection with the housing; a plurality of hollow gas permeable fibers adapted to permit (Continued)

diffusion of gas between blood and an interior of the hollow gas permeable fibers, the plurality of hollow gas permeable fibers being positioned between the blood flow inlet and the blood flow outlet such that blood flows around the plurality of hollow gas permeable fibers when flowing from the blood flow inlet to the blood flow outlet; a gas inlet in fluid connection with the housing and in fluid connection with inlets of the plurality of hollow gas permeable fibers; a gas outlet in fluid connection with the housing and in fluid connection with outlets of the plurality of hollow gas permeable fibers; and at least one moving element to create velocity fields in blood flow contacting the plurality of hollow gas permeable fibers. The plurality of hollow gas permeable fibers may extend generally perpendicular to the direction of bulk flow of blood through the housing.

20 Claims, 10 Drawing Sheets

Related U.S. Application Data

(60) Provisional application No. 61/730,581, filed on Nov. 28, 2012.

(51) Int. Cl.
| | | |
|---|---|---|
| *A61M 1/26* | (2006.01) | |
| *A61M 60/419* | (2021.01) | |
| *A61M 60/113* | (2021.01) | |
| *A61M 60/205* | (2021.01) | |
| *A61M 60/40* | (2021.01) | |
| *A61M 60/82* | (2021.01) | |
| *A61M 60/818* | (2021.01) | |

(52) U.S. Cl.
CPC .......... *A61M 1/267* (2014.02); *A61M 60/113* (2021.01); *A61M 60/205* (2021.01); *A61M 60/40* (2021.01); *A61M 60/419* (2021.01); *A61M 60/818* (2021.01); *A61M 60/82* (2021.01); *A61M 2205/7536* (2013.01); *A61M 2206/20* (2013.01)

(58) Field of Classification Search
CPC .............. A61M 1/1006; A61M 1/1015; A61M 1/1013; A61M 1/1029; A61M 1/1036; A61M 1/101; A61M 2206/20; A61M 2205/7536
See application file for complete search history.

(56) References Cited

U.S. PATENT DOCUMENTS

| | | | |
|---|---|---|---|
| 5,290,236 A | | 3/1994 | Mathewson |
| 5,399,074 A | * | 3/1995 | Nose .................. A61M 60/419 417/423.1 |
| 5,591,404 A | | 1/1997 | Mathewson |
| 5,695,471 A | * | 12/1997 | Wampler .............. F16C 39/063 604/131 |
| 5,770,149 A | | 6/1998 | Raible |
| 5,863,501 A | * | 1/1999 | Cosentino ........... A61M 1/1625 422/48 |
| 6,224,829 B1 | | 5/2001 | Piplani |
| 6,379,618 B1 | | 4/2002 | Piplani |
| 6,503,450 B1 | | 1/2003 | Afzal |
| 6,623,475 B1 | | 9/2003 | Siess |
| 6,723,284 B1 | | 4/2004 | Reeder |
| 2002/0110485 A1 | | 8/2002 | Stringer |
| 2007/0249888 A1 | | 10/2007 | Wu |
| 2008/0199357 A1 | * | 8/2008 | Gellman ............. A61M 1/1698 422/48 |

FOREIGN PATENT DOCUMENTS

| | | | |
|---|---|---|---|
| WO | WO1993005828 A2 | 4/1993 | |
| WO | WO199959654 A1 | 11/1999 | |
| WO | WO2006031858 A1 | 3/2006 | |
| WO | WO-2009100336 A1 * | 8/2009 | ............ A61M 37/00 |
| WO | WO2009100336 A1 | 8/2009 | |
| WO | WO2014085620 | 6/2014 | |

OTHER PUBLICATIONS

Zhang J, et al., . Characterization of membrane blood oxygenation devices using computational fluid dynamics. J. Membrane Sci 288:268-279, 2007.
Svitek RG, et al.; A mathematical model to predict CO2 removal in hollow fiber membrane oxygenators. Ann. Biomed. Eng. 36(6):992-1003, 2008.
Burgreen GW, Kameneva K. Hemolysis minimization using CFD-based design technology. ASAIO J. 50(2):171, 2004.
Zhang T, Wei X, Bianchi G, Wong P, Biancucci B, Griffith B, Wu Z. A novel wearable pump-lung device: In vitro and acute in vivo study. J Heart and Lung Transplant. 31(1): 101-105, 2012.
Whelan DM, Giessen WJ, Krabbendam SC, Vliet EA, Verdouw PD, Serruys PW, Beusekom HMM. Biocompatibility of phosphorylcholine coated stents in normal porcine coronary arteries. Heart, 83:338-345. 2000.
Hiromi Kitano, Hisatomo Suzuki, Kazuhiro Matsuura, and Kohji Ohno,,, Molecular recognition at the exterior surface of a zwitterionic telomer brush. Langmuir, 26(9):6767-6774.2010.
Yang W, Xue H, Carr LR, Wang J, Jiang S, Zwitterionic poly(carboxybetaine) hydrogels for glucose biosensors in complex media. Biosensors and Bioelectronics, 26:2454-245.2011.
Oh HI, Ye SH, Johnson CA JR, Woolley JR, Federspiel WJ and Wagner WR. Hemocompatibility assessment of carbonic anhydrase modified hollow fiber membranes for artificial lungs. Artificial Organs, 34(5):439-442. 2010.
Holmlin RE, Chen X, Chapman RG, Takayama S, Whitesides GM. Zwitterionic SAMs that resist nonspecific adsorption of protein from aqueous buffer. Langmuir, 17:2841-2850, 2001.
Okamoto T, Tashiro M, Sakanashi Y, et al.: A New Heparin-Bonded Dense Membrane Lung Combined with Minimal Systemic Heparinization Prolonged Extracorporeal Lung Assist in Goats. Artif Organs 22: 864-872, 1998.

* cited by examiner

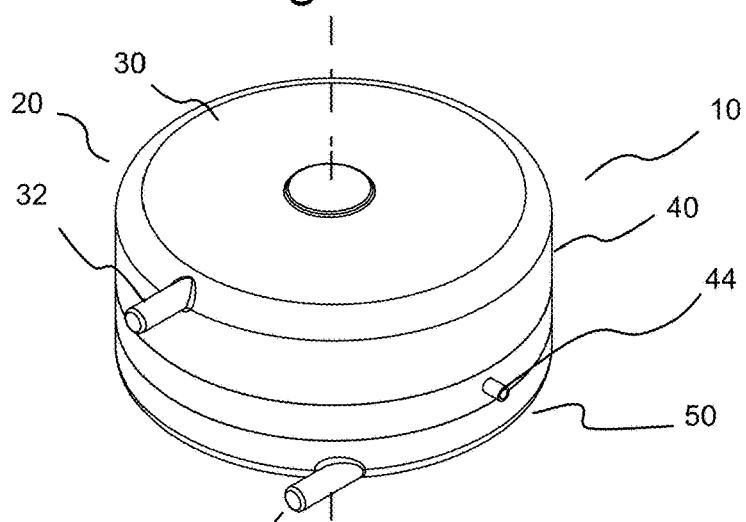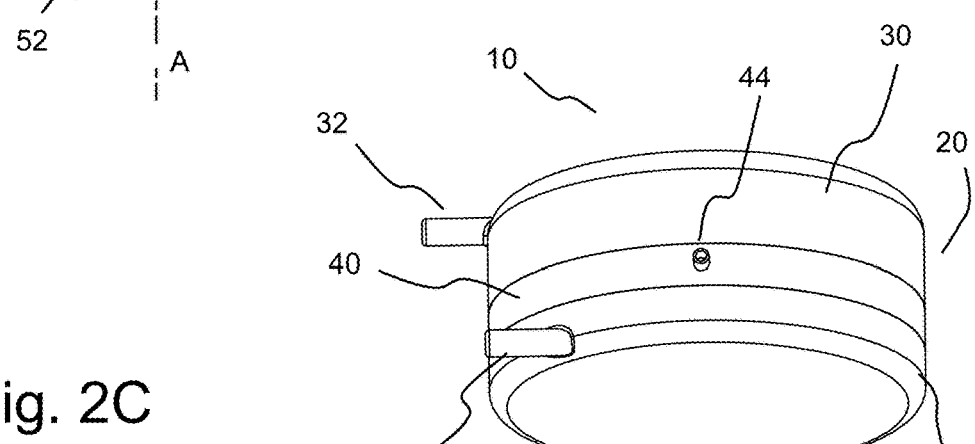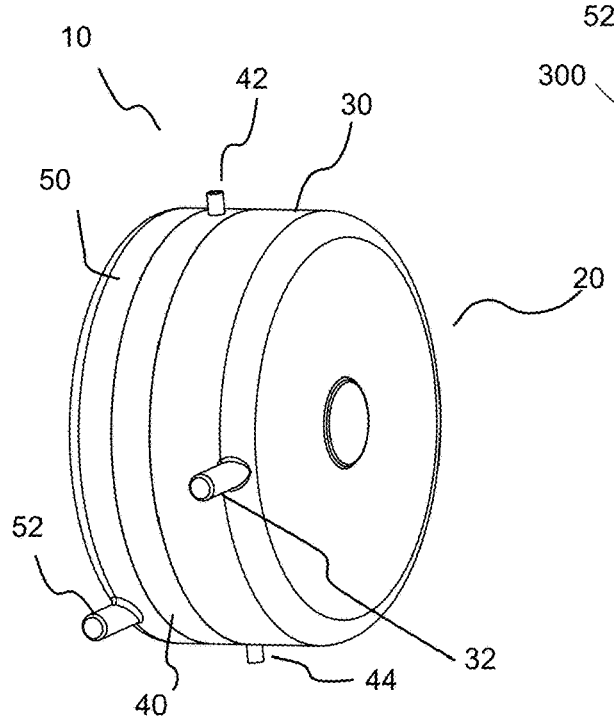

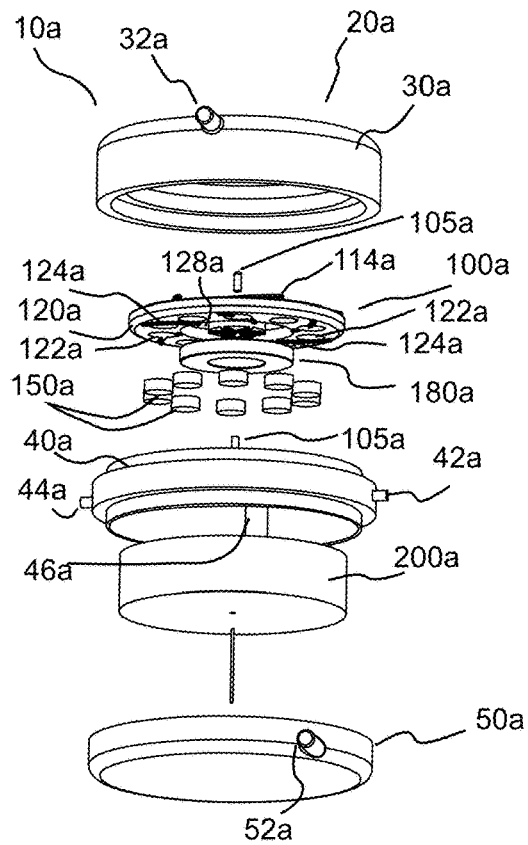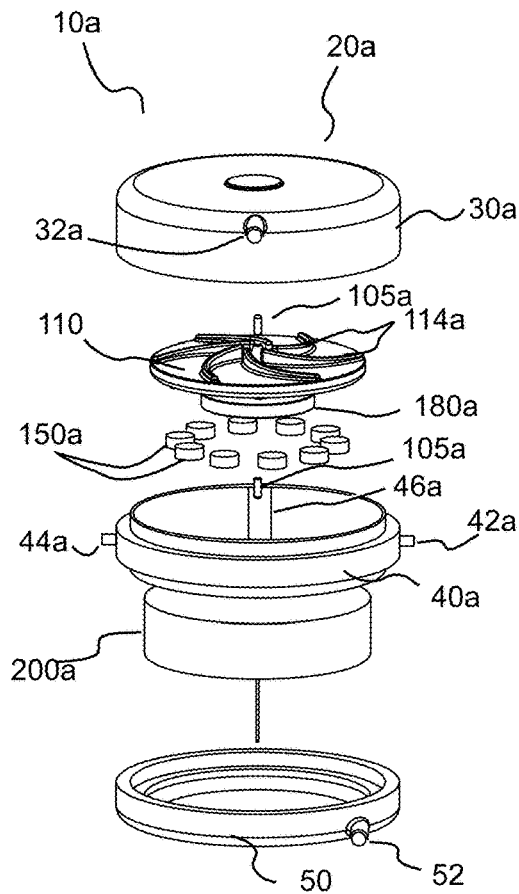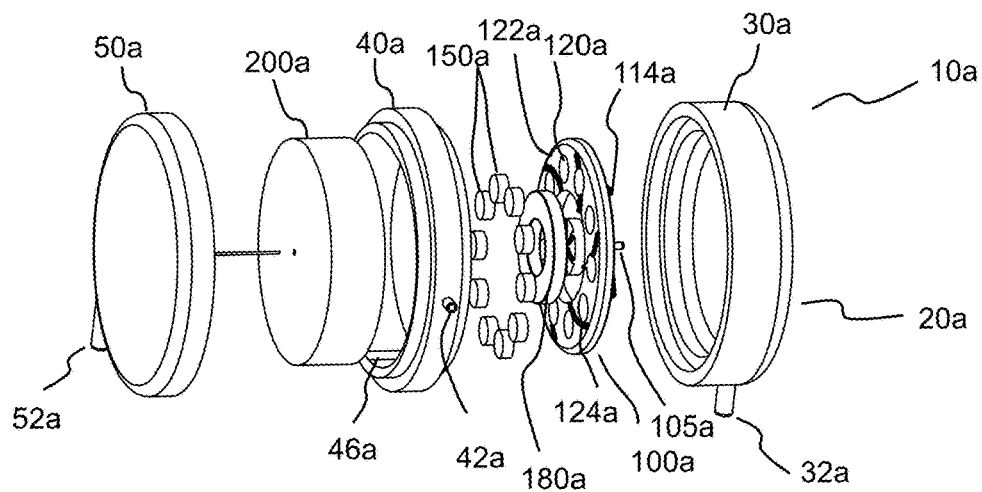

EXTRACORPOREAL AMBULATOR ASSIST LUNG

CROSS-REFERENCE TO RELATED APPLICATIONS

This application is a continuation application of U.S. patent application Ser. No. 14/647,861, filed May 28, 2015, which is a national phase filing of PCT International Patent Application No. PCT/US2013/072286, filed Nov. 27, 2013, which claims benefit of U.S. Provisional Patent Application Ser. No. 61/730,581, filed Nov. 28, 2012, the disclosures of which are incorporated herein by reference.

GOVERNMENTAL INTEREST

This invention was made with government support under grant number HL117637 awarded by the National Institutes of Health. The government has certain rights in the invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Acute and chronic diseases of the lung remain major healthcare problems. The American Lung Association reports that nearly 350,000 Americans die each year of some form of lung disease. Lung disease is the number three killer of Americans and is responsible for one in seven deaths. Acute lung failure and adult respiratory distress syndrome (ARDS) are prevalent forms of lung disease. ARDS afflicts about 150,000 Americans each year. The associated mortality of ARDS remains between 40 and 60% despite improvements in critical care medicine. Most lung disease, however, is chronic. Emphysema and chronic bronchitis, two forms of chronic obstructive pulmonary disease (COPD), afflict over 14 million Americans annually. Chronic lung disease is now the 3rd leading cause of death in America, claiming the lives of over 400,000 annually and carrying a cost of $154 billion. As chronic lung disease reaches end stage, lung transplantation becomes the only choice for effective treatment. Lung transplantation has had a steady rise over the last 10 years and 3300 lung transplants are performed annually worldwide. The average time on the waiting list varies from 6 to 12 months depending on the patient's condition and institutional expertise, and 10-15% of patients die while on the waiting list in the US. A narrow window of opportunity exists for lung transplant in any patient who is sick enough to benefit from the operation, but healthy enough to survive months of waiting for a donor lung and then the subsequent surgery.

Once they reach a critical condition, mechanical ventilation and extracorporeal membrane oxygenation (ECMO) are the only alternatives for respiratory support available to bridge acute and chronic respiratory patients to lung recovery or lung transplantation. Mechanical ventilation (MV) may maintain adequate gas exchange for short term support, but in longer term support can lead to ventilator induced lung injury from barotrauma (high pressure), volutrauma (over-distension), and biotrauma (molecular and cell mediated inflammation), which can further worsen the respiratory status of the patient. ECMO is expensive and complicated, requiring the use of an external pump and blood circuit that have to be supervised continuously by highly trained technicians. The confinement of the patient in MV and especially ECMO leads to a progressive deconditioning that is reflected in higher postoperative complications and earlier mortality after transplant. Nevertheless, ECMO has been increasingly considered as the only alternative to bridge patients to lung transplant or lung recovery after an acute decompensation from their disease. More recently, with increasing experience at active transplant centers and improvement in ECMO technology, the concept of "ambulatory ECMO" has gained popularity and facilitates and expedites patient recovery after transplantation. Success in ambulatory ECMO underscores the importance of maintaining patient mobility. Currently available ambulatory ECMO systems combine existing blood pumps and bypass oxygenators into an integrated system, but remain bulky and cumbersome and require frequent exchange of the oxygenators for longer term support.

Recent success with paracorporeal left ventricular assist devices (VADs) for heart failure patients has stimulated envisioning an ambulatory pump-lung device that can be a bridge to lung transplant or recovery. No fully integrated ambulatory pump-lungs are being used clinically, however. Portable or ambulatory systems under development integrate a separate blood pump and oxygenator under a single controller unit, but remain cumbersome. In such devices, a blood pump is typically connected by one or more conduits (for example, lengths of tubing) to an oxygenator. While a number of systems have integrated blood pumps, the blood leaving the impeller unit of these devices typically travels through channels before being distributed by manifolds into the hollow fiber bundle compartment.

SUMMARY

In one aspect, an extracorporeal (for example, a paracorporeal) system for lung assist includes a housing, a blood flow inlet in fluid connection with the housing; a blood flow outlet in fluid connection with the housing; a plurality of hollow gas permeable fibers adapted to permit diffusion of gas between blood and an interior of the hollow gas permeable fibers. The plurality of hollow gas permeable fibers are positioned between the blood flow inlet and the blood flow outlet such that blood flows around the plurality of hollow gas permeable fibers when flowing from the blood flow inlet to the blood flow outlet. The system further includes a gas inlet in fluid connection with the housing and in fluid connection with inlets of the plurality of hollow gas permeable fibers; a gas outlet in fluid connection with the housing and in fluid connection with outlets of the plurality of hollow gas permeable fibers; and at least one moving element to create velocity fields (that is, velocity field associated with the moving element or disturbed velocity fields) in blood flow contacting the plurality of hollow gas permeable fibers. The plurality of hollow gas permeable fibers may, for example, extend generally perpendicular to the direction of bulk flow of blood through the housing. Blood may be blocked from flowing to the gas inlet and the gas outlet.

The at least one moving element may, for example, include a rotating element. The rotating element may, for example, be provided with vanes and/or other extending elements (for example, axially extending elements) to enhance velocity fields created thereby. In a number of embodiments, the at least one moving element includes a rotating impeller adapted to pump blood from the blood flow inlet to the blood flow outlet. In a number of embodiments, the rotating impeller rotates in a plane generally parallel (that is, within no more than 5 degrees or within no more than 2.5 degrees of parallel) to an orientation of the hollow gas permeable fibers. In a number of embodiments, a surface of the rotating impeller is directly adjacent the plurality of hollow gas permeable fibers or fiber bundle. The surface of the rotating impeller adjacent the plurality of hollow gas permeable fibers may, for example, include vanes and/or other extending elements to enhance velocity fields created thereby. The impeller may, for example, include a disk, a first plurality of vanes on a first side of the disk and a second set of vanes or extending elements on a second side of the disk. The rotation of the impeller (or other rotating element) causes active mixing within the plurality of hollow gas permeable fibers. In a number of embodiments, the impeller includes a plurality of magnets in operative connection therewith and the system further comprises a magnetic drive system.

A spinning or rotating impeller or other element produces active blood mixing as a result of the swirling flow from the impeller penetrating into the fiber bundle. Active mixing refers generally to an increase in mass transfer efficiency of the lung compartment by disturbing the velocity fields contacting hollow fiber membranes. The increased exchange efficiency can reduce the required fiber surface area and priming volume, allowing the lung compartment of the system and overall system to be more compact. In a number of embodiments, a first stage (that is, a side of opposite the side adjacent the fiber bundle) of the impeller imparts centrifugal momentum to the blood that enters from the blood flow inlet (for example, directly to the center of the impeller. The second stage (that is, the side adjacent the fiber bundle) distributes the blood over the fiber bundle and converts the momentum imparted into pressure to drive axial flow through the lung compartment.

In a number of embodiments, the plurality of hollow gas permeable fibers is formed in at least one generally cylindrical bundle. The generally cylindrical bundle may, for example, be formed from a plurality of layers of fiber fabric (that is, a generally planar array, membrane of fabric of hollow gas permeable fibers). Each of the plurality of layers of fiber fabric includes hollow gas permeable fibers oriented in generally the same direction. Adjacent layers of fiber fabric may, for example, be rotated relative to each other such that the orientation of the plurality of hollow gas permeable fibers in adjacent layers of fiber fabric are of a different orientation.

In a number of embodiments, a first seal is formed between the generally cylindrical bundle and the housing at a first position, and a second seal is formed between the generally cylindrical bundle and the housing at a second position, rotated around the circumference of the generally cylindrical bundle from the first position, to form a gas inlet manifold in fluid connection with the gas inlet on a first side of the first seal and the second seal and a gas outlet manifold in fluid connection with the gas outlet on a second side of the first seal and the second seal. The first seal and the second seal block fluid connection between the gas inlet manifold and the gas outlet manifold.

The system may, for example, further include a moving/rotating element positioned within the housing adjacent to the plurality of hollow gas permeable fibers on an opposite side thereof of the impeller. The rotating element may, for example, include a second impeller. In systems including a plurality of fiber bundles, one or more moving/rotating element may, for example, be placed between adjacent fiber bundles.

The plurality of hollow gas permeable fibers may, for example, include at least one species of zwitterionic molecule attached to or tethered on surfaces thereof. The plurality of hollow gas permeable fibers may include heparin attached to or tethered on surfaces thereof.

In a number of embodiments, the system further includes a system to offset hydrodynamic force. For example, the system to offset hydrodynamic force may include a first magnet in operative connection with the impeller which cooperates with a second magnet to create a repellant force therebetween. In embodiments including a magnetic drive, such a system may be used to offset both hydrodynamic force and magnetic coupling force between the plurality of magnets and the magnetic drive.

The system may, for example, be adapted to deliver flows in the range or approximately 2 to 4 liters per minute. The flow or flow rate may, for example, be adjustable (for example, by varying the speed of an impeller) to, for example, adjust to varying requirements in lung assist.

The system may, for example, further include a first pivot bearing on a first side of the moveable element (for example, an impeller) and a second pivot bearing on a second side of the moveable element.

In a number of embodiments, the moveable element (for example, an impeller) includes one more holes or passages therethrough.

The system may, for example, further include at least a second plurality of hollow gas permeable fibers (for example, a second, generally cylindrical fiber bundle) spaced from the (first) plurality of hollow gas fibers set forth above. The second plurality of hollow gas permeable fibers is adapted to permit diffusion of gas between blood and an interior of the second plurality of hollow gas permeable fibers. The second plurality of hollow gas permeable fibers is spaced from the plurality of hollow gas permeable fibers between the blood flow inlet and the blood flow outlet such that blood flows around the second plurality of hollow gas permeable fibers when flowing from the blood flow inlet to the blood flow outlet. The second plurality of hollow gas permeable fibers may extend generally perpendicular to the direction of bulk flow of blood through the housing. The gas inlet is in fluid connection with inlets of the second plurality of hollow gas permeable fibers. The gas outlet is in fluid connection with outlets of the second plurality of hollow gas permeable fibers. The system may further include at least a second moving element (for example, a second impeller) to create velocity fields in blood flow contacting the second plurality of hollow gas permeable fibers positioned between the plurality of hollow gas permeable fibers and the second plurality of hollow gas permeable fibers. One or more additional pluralities of hollow gas permeable fibers may be provided in series. Additional moveable element (for example, impellers) may be provided between adjacent pluralities of hollow gas permeable fibers to create velocity fields/active mixing.

In another aspect, a method for extracorporeal (for example, paracorporeal) lung assist includes providing a plurality of hollow gas permeable fibers within a housing, the plurality of hollow gas permeable fibers being adapted to permit diffusion of gas between blood and an interior of the hollow gas permeable fibers, the plurality of hollow gas permeable fibers being positioned between a blood flow inlet and a blood flow outlet such that blood flows around the plurality of hollow gas permeable fibers when flowing from the blood flow inlet to the blood flow outlet; flowing a sweep gas including oxygen through the plurality of hollow gas permeable fibers; and moving at least one movable element to create velocity fields (that is, velocity field associated with the moving element or disturbed velocity fields) in blood flow contacting the plurality of hollow gas permeable fibers. In a number of embodiment, the plurality of hollow gas permeable fibers extend generally perpendicular to the direction of bulk flow of blood through the housing. The method may, for example, further include element or actions as described above.

In a further aspect, an extracorporeal (for example, paracorporeal) system for lung assist include a housing, a blood flow inlet in fluid connection with the housing, a blood flow outlet in fluid connection with the housing, a plurality of hollow gas permeable fibers adapted to permit diffusion of gas between blood and an interior of the hollow gas permeable fibers, the plurality of hollow gas permeable fibers being positioned between the blood flow inlet and the blood flow outlet such that blood flows around the plurality of hollow gas permeable fibers when flowing from the blood flow inlet to the blood flow outlet, a gas inlet in fluid connection with the housing and in fluid connection with inlets of the plurality of hollow gas permeable fibers, a gas outlet in fluid connection with the housing and in fluid connection with outlets of the plurality of hollow gas permeable fibers. at least one moving element to create velocity fields in blood flow contacting the plurality of hollow gas permeable fibers, a first pivot bearing on a first side of the moveable element, and a second pivot bearing on a second side of the moveable element. Blood entering the housing may, for example, flow across the first pivot bearing and the second pivot bearing to flush a surface of the first pivot bearing and a surface of the second pivot bearing.

The present devices, systems and methods, along with the attributes and attendant advantages thereof, will best be appreciated and understood in view of the following detailed description taken in conjunction with the accompanying drawings.

BRIEF DESCRIPTION OF THE DRAWINGS

FIG. 2A illustrates a perspective, assembled view of the system of FIG. 1A.

FIG. 2B illustrates another perspective, assembled view of the system of FIG. 1A including a schematic representation of a magnetic drive system.

FIG. 2C illustrates another perspective, assembled view of the system of FIG. 1A.

FIG. 3E illustrates a perspective, exploded view of another embodiment of a paracorporeal ambulatory assist lung system hereof.

FIG. 3F illustrates another perspective, exploded view of the system of FIG. 3E.

FIG. 3G illustrates another perspective, exploded view of the system of FIG. 3E.

DETAILED DESCRIPTION

Figure 1A:
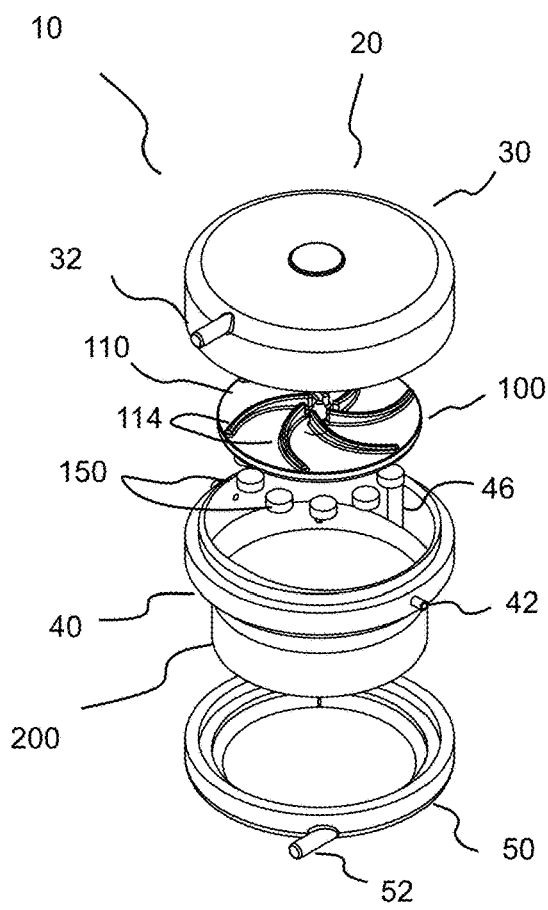
FIG. 1A illustrates a perspective, exploded view of an embodiment of a paracorporeal ambulatory assist lung system hereof.
Figure 1B:
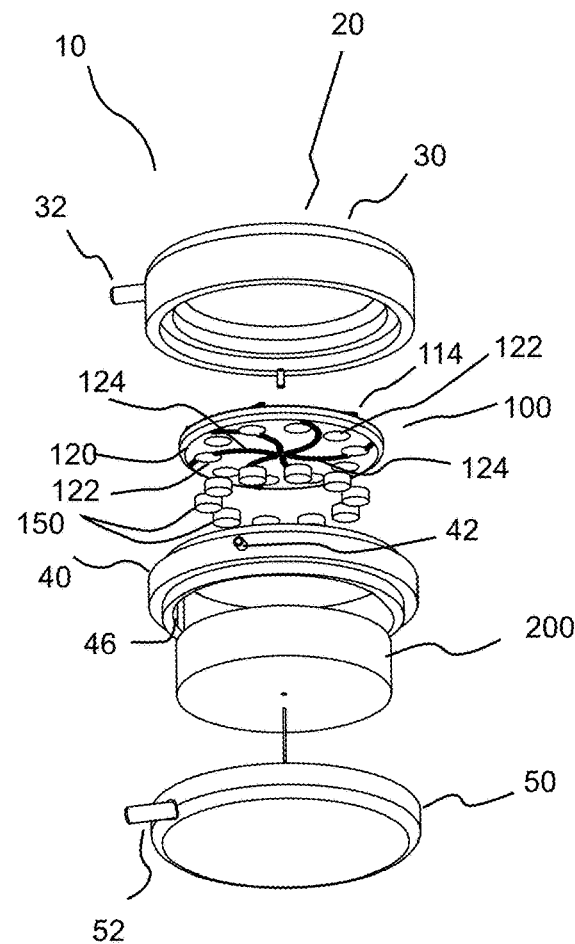
FIG. 1B illustrates another perspective, exploded view of the system of FIG. 1A.
Figure 1C:
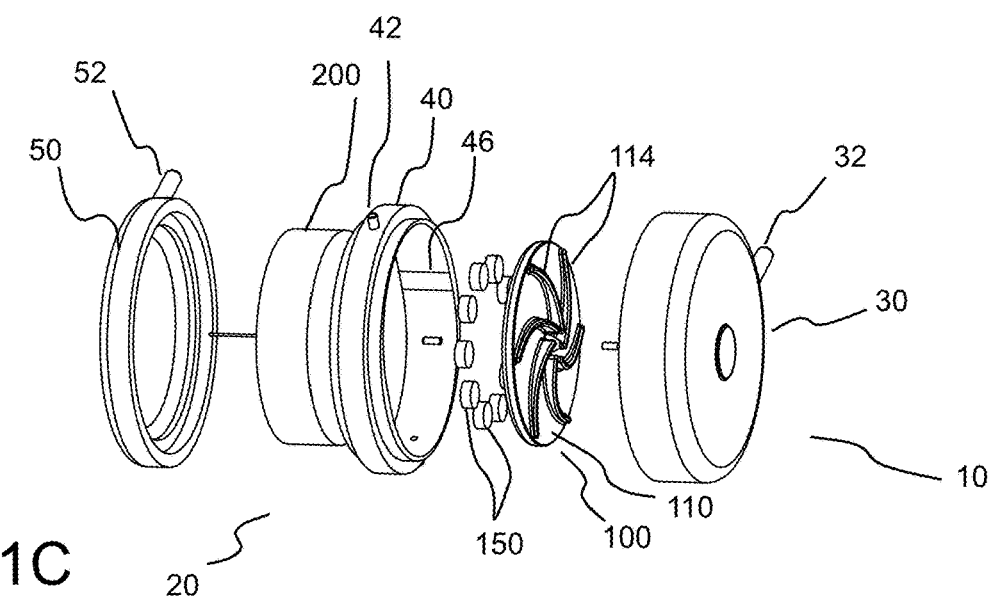
FIG. 1C illustrates another perspective, exploded view of the system of FIG. 1A.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an impeller" includes a plurality of such impellers and equivalents thereof known to those skilled in the art, and so forth, and reference to "the impeller" is a reference to one or more such impellers and equivalents thereof known to those skilled in the art, and so forth. Recitation of ranges of values herein are merely intended to serve as a shorthand method of referring individually to each separate value falling within the range. Unless otherwise indicated herein, each separate value and intermediate ranges are incorporated into the specification as if individually recited herein. All methods described herein can be performed in any suitable order unless otherwise indicated herein otherwise clearly contraindicated by the text.

In a number of embodiments, extracorporeal/paracorporeal ambulatory assist lung system hereof provide advantages in gas transfer efficiency and biocompatibility. The systems hereof may, for example, be designed for either central and/or peripheral cannulation and respiratory support of, for example, 1-3 months duration before device change-out may be required. Systems hereof are, for example, amenable to patients suffering from severe acute respiratory failure (ARDS) to chronic patients suffering from COPD or severe pulmonary hypertension (PH). Paracorporeal device or systems are extracorporeal devices generally located immediately adjacent to the body during use. In other words, paracorporeal devices or systems are "wearable" or ambulatory devices or systems. The systems hereof are well suited for paracorporeal/ambulatory use as well as use as generally stationary extracorporeal systems.

The system hereof are less cumbersome than ambulatory ECMO systems currently under development while providing for increased ambulatory respiratory assist. In a number of embodiments, systems hereof provide a highly integrated blood pump and lung, in which a pump mechanism such as an impeller spins adjacent to a plurality of hollow gas permeable fibers (sometimes referred to herein as a fiber bundle). Systems hereof may, for example, be designed to be worn in a holster or vest paracorporeally. Directly integrated an impeller or other moving/rotating element adjacent to the fiber bundle enables impeller rotation to enhance gas exchange. In a number of embodiments, the impeller of the system hereof is magnetically driven, but does not require magnetic levitation, resulting in a lighter, less complex, and less expensive system.

In a number of embodiments of system 10 hereof as illustrated in FIGS. 1A through 3C, system 10 includes a housing 20 including a rotating element such as a rotating impeller 100 therein, which is, for example, positioned directly adjacent (for example, subjacent in the normal orientation of operation as illustrated in FIG. 3 without intervening flow altering elements) to fiber bundle 200. Housing 20 is formed in multiple sections (three sections in the illustrated embodiment) including a first end section 30, an intermediate section 40 and a second end section 50. A blood flow inlet 32 is formed in connection with first end section 30, and a blood flow outlet 52 is formed in connection with second end section 50. Intermediate section 40 includes a gas flow inlet 42 and a gas flow outlet 44.

Figure 3A:
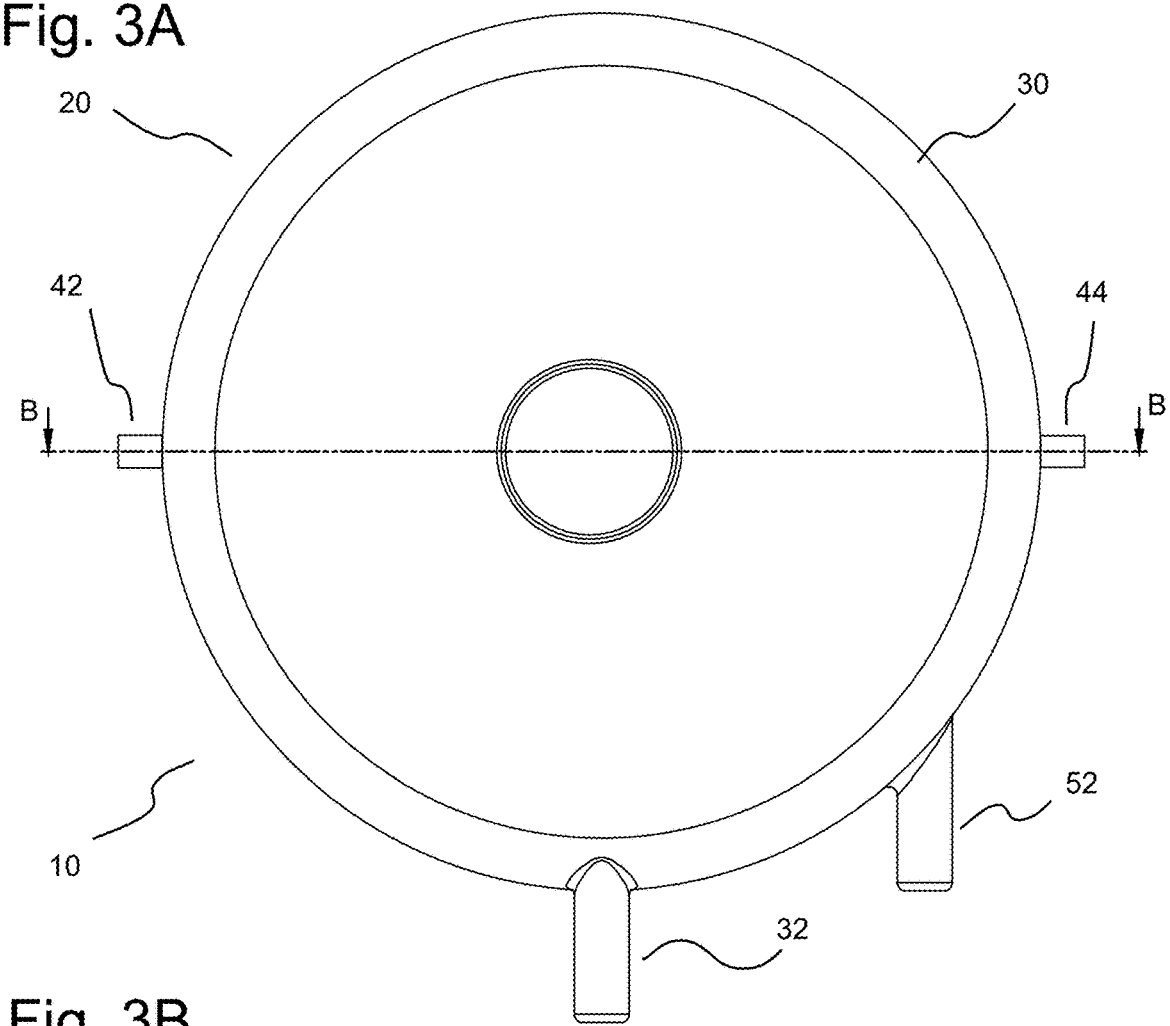
FIG. 3A illustrates a top plan view of the system of FIG. 1A.
Figure 3B:
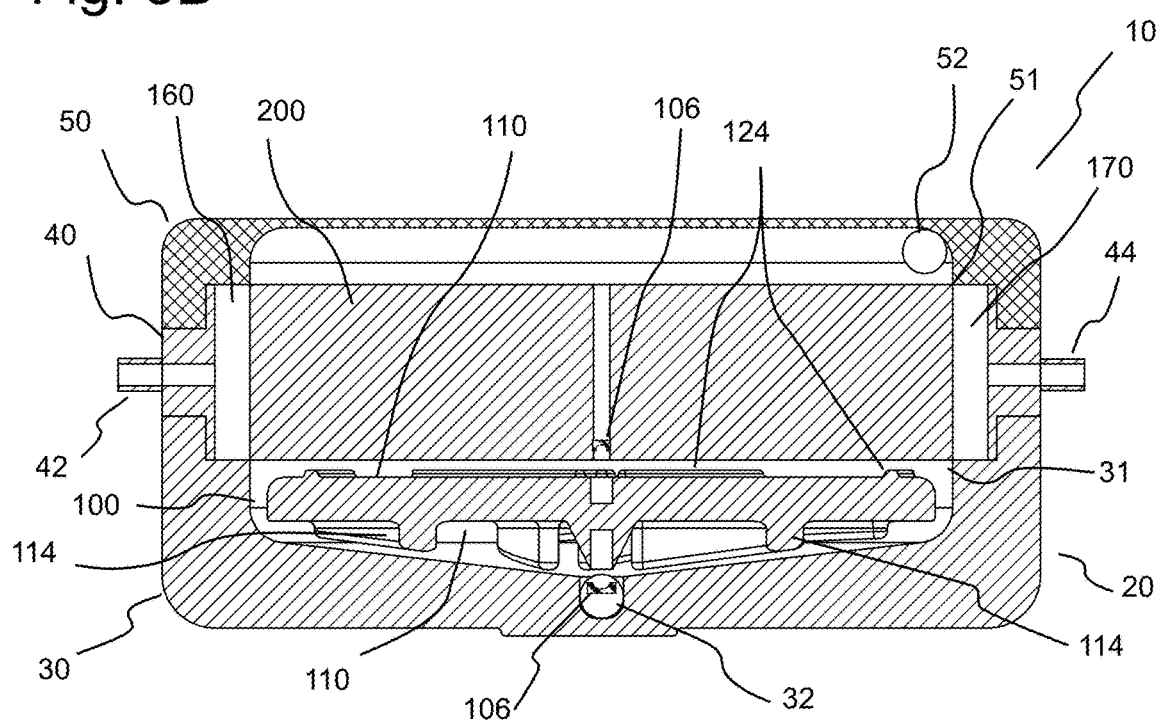
FIG. 3B illustrates a cross-sectional view of the system of FIG. 1A along section B-B of FIG. 3A.

As, for example, illustrated in FIG. 3B, first end section 30, intermediate section 40 and second end section 50 are connected to form integral housing 20. In the illustrated embodiment, impeller 100 has generally the same diameter as fiber bundle 200 and is positioned directly adjacent fiber bundle 200. In a number of embodiments, there is, for example, no intervening extending conduit (for example, tubing, channels etc.) through which blood must flow from impeller 100 (or other moving or rotating element) to reach fiber bundle 200 or other flow restrictions or obstructions which would cause the viscosity of the fluid to significantly dampen the flow velocity fields created by impeller 100 or another rotating member. This arrangement produces "active blood mixing" wherein a disturbed flow field generated by rotating impeller 100 penetrates into fiber bundle 200, creating locally increased flow velocities. In general, "active mixing" refers to increasing the mass transfer efficiency of the lung compartment by disturbing the velocity fields contacting hollow fiber membranes thereof. Such active mixing reduces diffusional boundary layers at the fiber surfaces and results in increased gas exchange.

In that regard, a spinning impeller/surface creates velocity disturbances, $V_d$, in the blood flow path that scale as $V_d \sim 2\pi f D/2$, where f is the impeller rotational frequency and D is the impeller diameter. These velocity disturbances are in addition to and can be 10-1000 times greater than the average velocity $V_{avg}$ of blood flow through the hollow fiber bundle and are responsible for "active mixing" that enhances gas exchange. The placement of the fiber bundle, for example, directly adjacent to the spinning impeller/surface allows the disturbances to be convected into the fiber bundle and produce the active mixing. In a number of embodiments, systems hereof do not include channels, pathways, or any other flow directing structures between the impeller and fiber bundle that would dampen the impeller generated velocity disturbances. If L is the distance from the impeller to the fiber bundle and d is the characteristic minimum transverse dimension (i.e. perpendicular to the direction of net flow) of channels, pathways, or other flow directing structures between the impeller and fiber bundle, then the velocity disturbances will be convected to the fiber bundle only if the transit time from the impeller to the fiber bundle is much less than the time for transverse diffusion of momentum across the channels, pathways etc. In a number of embodiments, $$\frac{L}{\overline{V}} \ll \frac{d^2}{v}$$

where $\overline{V}$ is the mean blood flow velocity towards the fiber bundle in the channels, pathways, or flow directing structures and v is the kinematic velocity of blood. The open space between the impeller and fiber bundle (large d) and the placement of the impeller adjacent to the fiber bundle (small L) in the systems hereof maximizes the propagation of the impeller-generated flow disturbances to the fiber bundle. In a number of embodiments, the surface of the impeller or other moving/rotating element adjacent the fiber bundle is no more than 1 cm from the fiber bundle, no more than 2 mm from the fiber bundle or no more than 1 mm from the fiber bundle.

FIG. 3E through 3I illustrate another embodiment of a system 10a which is very similar in construction and operation to system 10. In system 10a, components are numbered similarly to like components of system 10 with the addition of the designation "a" thereto. During operation, the negative pressure generated in the system inlet region (that is, the space between impeller 100a and the inner wall of section 30a of housing 20a) results in a force applied on impeller 100a in the direction of section 30a of housing 20a. This hydrodynamic force, in addition to the force of ten coupling magnets 150a, can wear the bearing material (in the housing section 30a) and lead to pump failure over time. System 10a include a system to offset the combined hydrodynamic and coupling magnet forces. In the illustrated embodiment, a repelling magnet 180a is seated in a seating 128a of impeller 100a and (in cooperation with another magnet 190a (see FIG. 30 which may be external to housing 120a) is operable to apply force offset the combined hydrodynamic and coupling magnet forces, thereby minimizing the axial forces applied to the bearings, and improving overall system durability.

Figure 4:
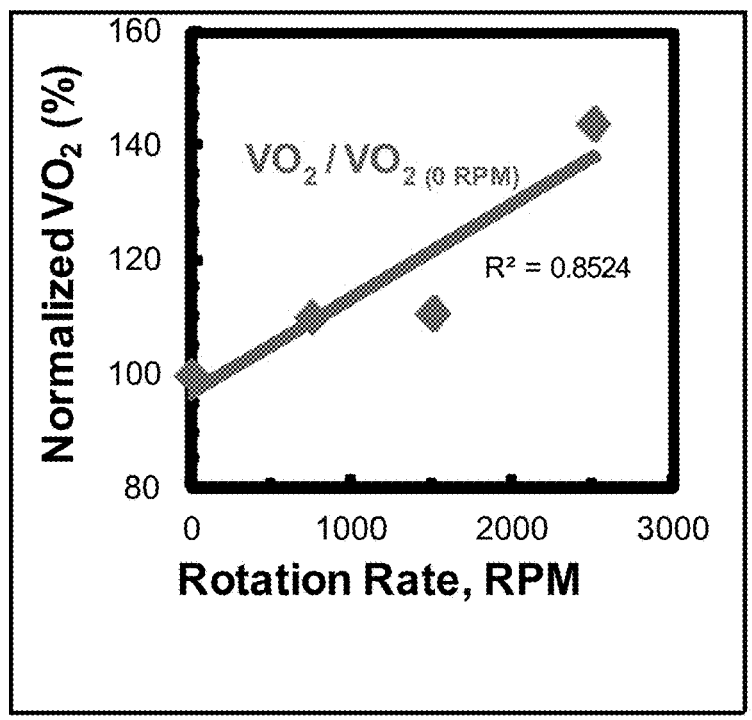
FIG. 4 illustrates the results of a study of normalized $VO_2$ as a function of impeller rotation rate.

FIG. 4 illustrates the effect of active mixing in system 10. We performed a standard gas exchange characterization of an embodiment of system 10 in blood using established testing standards. In several studies, the blood flowrate through system was a constant 3.3 LPM, which was set via a BIOMEDICUS® pump available from Medtronic of Minneapolis, Minn. in the test setup. The rotating speed of impeller 100 was varied from 0 (no pumping) to 2500 RPM (all pumping being performed by impeller 100). At a constant blood flowrate flowing through system 10, the rotation of impeller 100 increased gas exchange by 45% over the range of studied impeller rotating speeds (as compared to the case wherein there is no rotation). In systems in which an impeller is isolated from the fiber bundle via on or more interconnecting conduits/tubes impeller rotation will have no effect on gas exchange at a set constant blood flowrate through such systems. Active mixing allows for meeting gas exchange design requirements with less fiber surface area, leading potentially to a more compact system.

Even with active mixing, the fiber surface area of system 10 may, for example, be at least ~½ m² in a number of embodiments. Fiber bundle 200 may, for example, include thromboresistant fibers formed of a thin siloxane layer to prevent plasma wetting with a covalently attached heparin coating to decrease thrombogenicity. Suitable siloxane-heparin fibers have been developed by Alung Technologies of Pittsburgh, Pa. using the CELGARD® X-240 polypropylene (PP) fiber available from Celgard LLC of Charlotte, N.C. OXYPLUS® polymethylpentene (PMP) hollow fiber or capillary fabrics or membranes available from Membrana GmbH of Wuppertal, Germany may also, for example, be used.

PP fibers used in studies hereof had an outer diameter or OD of 300 micron and an inner diameter or ID of 240 micron. The PMP fibers had an OD of 380 micron and an ID of 200 micron. These fibers were manufactured as arrays, membranes or fabrics of hollow fibers, wherein a plurality of fibers are fabricates as an integral, generally planar array having generally the same fiber orientation. In forming fiber bundle 200, such arrays, membranes or fabrics are cut into sheets that were placed one on top of the other in stack of multiple layers (62 layers in the studied embodiments of fiber bundle 200) such that the overall surface area for gas exchange was maintained at 0.85 m². The porosity of fiber bundle was maintained at 0.6. Upon formation, fiber bundle 200 had a diameter of 3.85 inches (0.0978 meters) and a height of 0.88 inches (0.0224 meters). The bundle diameter was such that it closely matched the impeller diameter (3.85 inches or 0.0978 meters).

As described above, the fibers used in the studies of system 10 were provided in array. fabric or membrane form. Other approaches to improving thromboresistance include the use of zwitterionic molecular species attached (for example, covalently) to the surface of the fibers without significantly affecting gas transport across the fiber surface. Furthermore, blood flow paths and patterns in system 10 may be optimized using for example computational fluid dynamics or CFD for improved hemocompatibility. The ultimate anticoagulation requirements for system 10 may also be further reduced because blood exiting system 10 flows through the patient's lungs, which can continue to act as a filter of small emboli.

As described above, blood enters system 10 through blood flow inlet or inlet port 32 and is pumped by radial impeller 100. In a number of studied embodiments, impellers 200 was supported by two pivot bearings 105 (for example, sapphire or ceramic pivot bearings) mounted into housing 20 and aligned with the central axis of radial impeller 100. As known in the bearing arts, pivot bearing 105 may for example, include a rounded end that rotatable relative to a bearing cup 106 (for example, similar to a ball and socket joint) as, for example, illustrated in FIG. 3B. Synthetic (ceramic) pivot bearings suitable for user herein are, for example, available from Swiss Jewel of Philadelphia. Bearing cups 106 were formed from ultrahigh molecular weights polyethylene and are available from Modern Plastics of Shelton, Conn. The use of pivot bearings 105 eliminate the need for seals and bearings. The pivot bearing maintain impeller 100 axially and radially aligned within system 10. Also, secondary saline infusion used in some systems to beep blood from contacting friction/heat generating components are not required. Fresh blood enters system 10 and flows across pivot bearings 105, continually flushing the area with fresh fluid.

Magnetically suspended or levitated impellers without bearings may, for example, be used to further increase longevity. However, system 10, in a number of embodiments, may require periodic change-out (for example, every 1-3 months) of system 10 as a result of fouling in the lung compartment. A simpler and less complex approach of magnetic coupling of impeller 100, but not magnetic levitation, was chosen in a number of embodiments. In the illustrated embodiment, magnets 150, which are seated in seatings 122 (see FIG. 1B), on rotating impeller 100 couple magnetically to rotating magnets on an external motor driver 300 (illustrated schematically in FIG. 2B) to maintain a hermetic seal. In a number of embodiments, impeller 100 was a two-stage impeller. The first stage of impeller 100 (on a first or blood-inlet side 110 of impeller 100) includes a first plurality of impeller vanes 114 and imparts centrifugal momentum to the blood that enters from the blood flow inlet 100 to impeller 100. The second stage (on a second or fiber-bundle side 120 of impeller 100) includes a second set of vanes 124 to distribute the blood over a surface of fiber bundle 200 and convert the momentum imparted to the blood into pressure to drive axial flow through the "lung compartment" formed by fiber bundle 200.

In the illustrated embodiment, the rotation of impeller 100 was counterclockwise, and the placement of vanes 114 was concave in the direction of rotation, such that a pumping action is created upon impeller rotation. Vanes 114 were designed such that the tip of each vane 114 formed a 30 degree angle to the tangent at the point where vane 114 intersects an outer diameter of that vane. The angle and other vane properties can be adjusted to alter the pumping efficiency of impeller 114. In a number of embodiment, second stage vanes 124 were mirror images of first stage vanes 114, and were convex in the direction of rotation. The vane curvature and/or other vane properties may, for example, be used to disturb velocity fields locally.

Figure 3C:
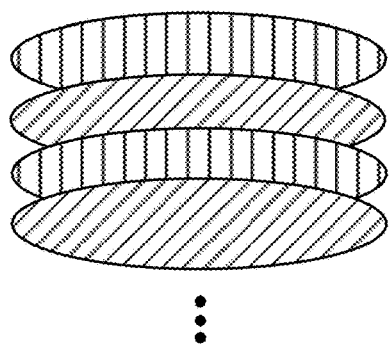
FIG. 3C illustrates a perspective, exploded view of various layers of an embodiment of a fiber bundle hereof wherein the orientation of the fibers in adjacent layers is rotated with respect to each other (wherein the fibers within individual layers are oriented in generally the same direction).

In a number of embodiments, fiber bundle 200 was a generally cylindrical bundle of hollow fiber membranes (for example, siloxane and heparin coated fiber arrays, membranes or fabrics as described above) stacked in layers at, for example, 5-15 degree angles to one another and aligned generally perpendicular to the principal direction of blood flow (that is, generally perpendicular to axis A of housing 20 or generally parallel to the plane of rotation (or radius) of impeller 100)—see FIGS. 2A and 3C) to maximize gas exchange. In a number of representative studied embodiments, fiber bundle 200 was a generally cylindrical bundle of hollow fiber membranes stacked in layers at approximately 7 degree angles to one another. The ends of the hollow fibers were potted into semi-circular gas manifolds (gas inlet manifold 160 and gas outlet manifold 170) located at the sides of system 10 in the orientation of, for example, FIG. 3B into which the fibers of fiber bundle opened.

Aligning the hollow fibers generally perpendicular (for example, within nor more 5 degrees from perpendicular or within nor more than 2.5 degrees of perpendicular) to axis A can significantly decrease volume (that is, improve compactness) as compared to systems in which hollow fibers are generally parallel to the axis of the housing. In such systems, an annular fiber bundle may be used, and a rotating element may be placed in the central annular opening. In the configurations described herein, impeller 100 or other movable/rotatable element can be placed very close to fiber bundle 200 and fiber bundle 200 can be made relatively thin to achieve/increase active mixing throughout the thickness or axial depth fiber bundle 200. Active mixing is, for example, limited to certain depth within the fiber bundle depending, for example, upon the nature of impeller and impeller rotational speed (which may be optimized). As described further below, multiple, relatively thin fiber bundles (with, for example, intervening rotating/moveable elements to effect active mixing) may be used in the systems hereof. Controlling, for example, fiber bundle properties (including, for example, axial depth or thickness, porosity, permeability etc.) and impeller properties (including, for example, physical properties, positional placement, quantity etc.) to provide for a predetermined or optimized amount of active mixing throughout the depth of one or more fiber bundles can be used to optimize efficiency and minimize, for example, volume of the lung compartment and/or blood trauma. Moreover, in the case of hollow fibers oriented generally perpendicular to axis A (or generally parallel to the plane of rotation of impeller 100), a relatively large impeller may be used to, for example, minimize bundle thickness and increase active mixing. As described herein, impeller 100 may, for example, have a diameter approximately equal to fiber bundle 200.

In a number of embodiments, fiber bundle 200 was sealed to axially extending sealing sections 46 formed on an inner wall of intermediate section 40 to form the generally semi-circular manifolds. Sealing sections 46 may, for example, extend radially inward to contact and form a sealing connection with fiber bundle 200. Two sealing section 46 were used to form generally semi-circular (that is, extending approximately 180 degrees) manifolds. Additional sealing sections may, for example, be used to create manifolds that extend around the inner circumference of housing 10 less than 180 degrees.

Fiber bundle 200 may, for example, be wound and positioned within a four-piece reusable mold made from, for example, acetal (Delrin) for potting. During potting, two-part polyurethane adhesive (available from Cas Chem, of Bayonne, N.J.) is injected into the mold. The mold is then centrifuged to assure even distribution around the periphery without any voids. Once the adhesive has cured, the potted fibers are removed and trimmed. This procedure establishes a common gas pathway between all fibers.

During operation, an oxygen-containing "sweep gas" (for example, oxygen) flows into gas inlet manifold 160 via gas flow inlet 42 and is distributed through the lumens of the individual fiber membranes of fiber bundle 200. Oxygen ($O_2$) diffuses out of the fibers into the flowing blood as carbon dioxide ($CO_2$) diffuses from blood into the fibers and is carried by the sweep gas to outlet manifold 170 and therethrough to gas flow outlet 44. As described above, the blood then leaves system 10 via blood flow outlet 52. Oxygen and carbon dioxide exit the lumens of the fibers into gas outlet manifold 170. As, for example, illustrated in FIG. 3B, an inner diameter or flange 31 of first end section 30 and an inner diameter of flange 51 of second end section 50 (see, FIG. 3B) are smaller than the inner diameter of intermediate section 40 to entrap fiber bundle 200 and form gas inlet manifold 160 and gas outlet manifold 170. In the illustrated embodiment, a lower end (in the illustrated orientation of FIG. 3B) or flange of first end section 30 contacts and forms a seal with an upper surface of fiber bundle 200. An upper end of flange or second end section 50 contacts and forms a seal with a lower surface of fiber bundle 200. Blood is thereby prevented from directly flowing into gas inlet manifold 160 and/or gas outlet manifold 170. The potting of fiber bundle 200 prevents blood flow flowing radially out of fiber bundle 200 and into gas inlet manifold 160 and/or gas outlet manifold 170.

Figure 5:
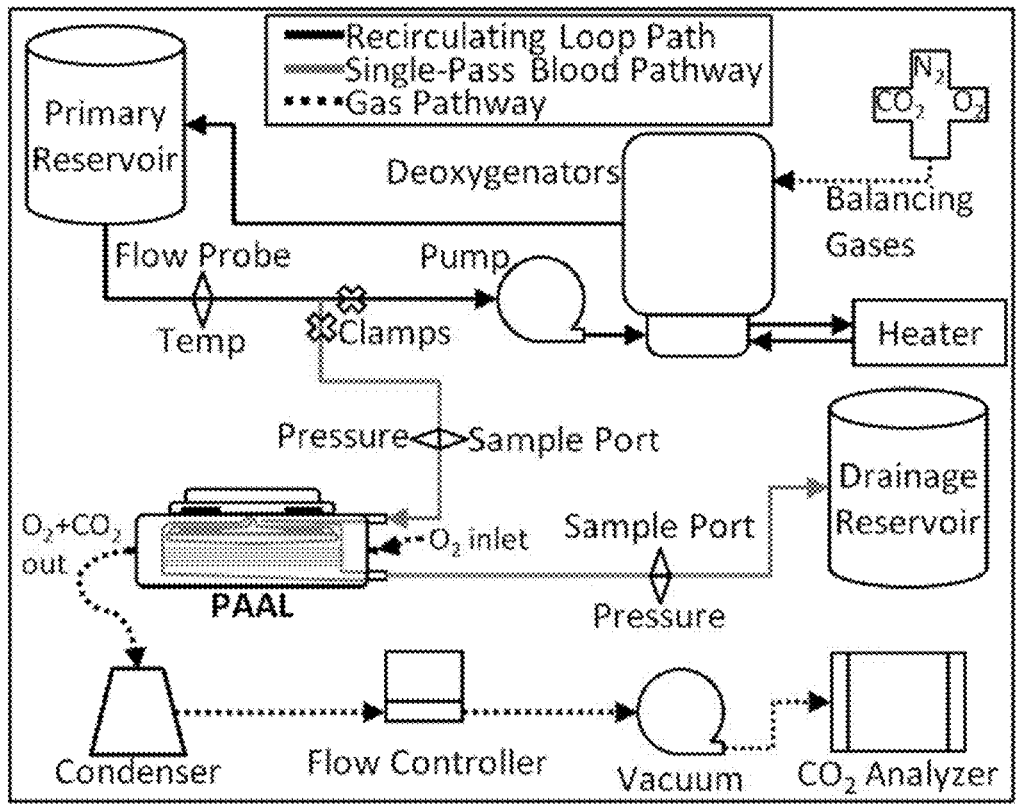
FIG. 5 illustrates an experimental setup for studying the systems hereof.
Figure 6:
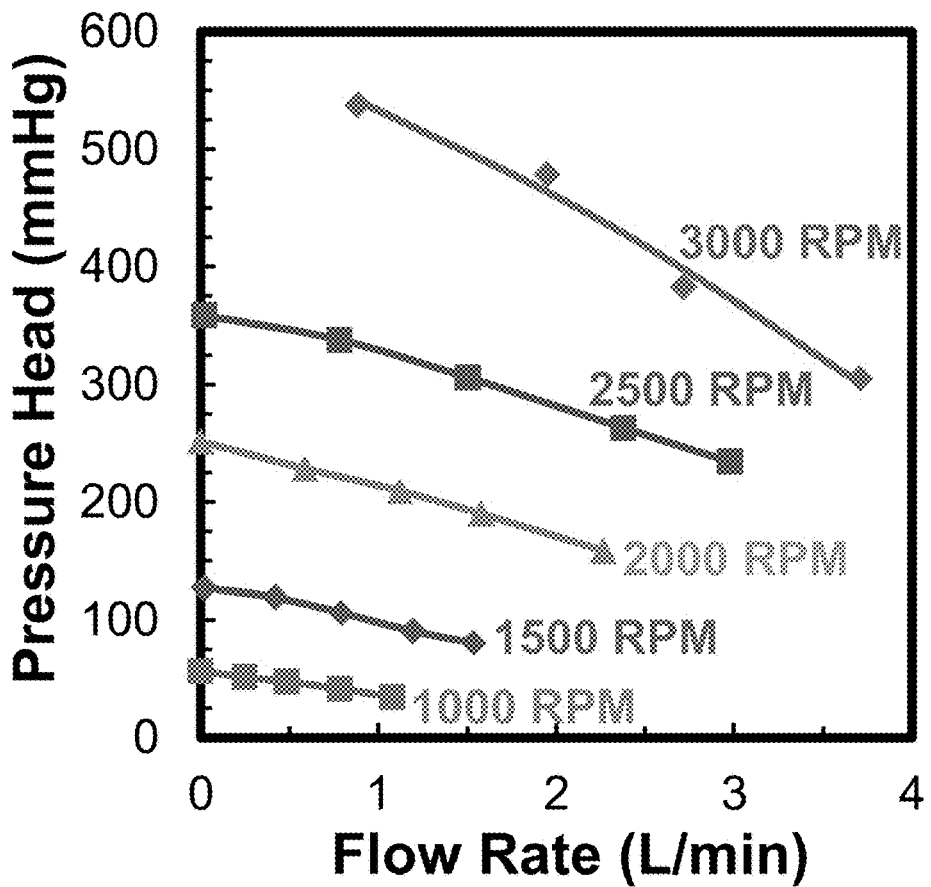
FIG. 6 illustrates pump curves showing the results of a study of pressure head as a function of flow rate at various rotational speeds.

Systems 10 used in studies hereof were not optimized. As further described below, optimization may be effected, for example, using a number of tools including CFD, bench testing and/or in vivo studies. FIG. 5 illustrates the experimental setup used in the studies hereof. FIG. 6 illustrates pump-flow curves for system 10 over a range of operating speeds in a blood analogue fluid with viscosity of 3.5 cP. Operating between 2000-3000 RPM, system 10 could deliver flows from 2-3.5 liters per minute or LPM while generating pressure heads from 200-500 mmHg. This dynamic range enables system 10 to be attached using peripheral and/or central placement modes using either access cannula or directly connecting grafts.

Figure 3D:
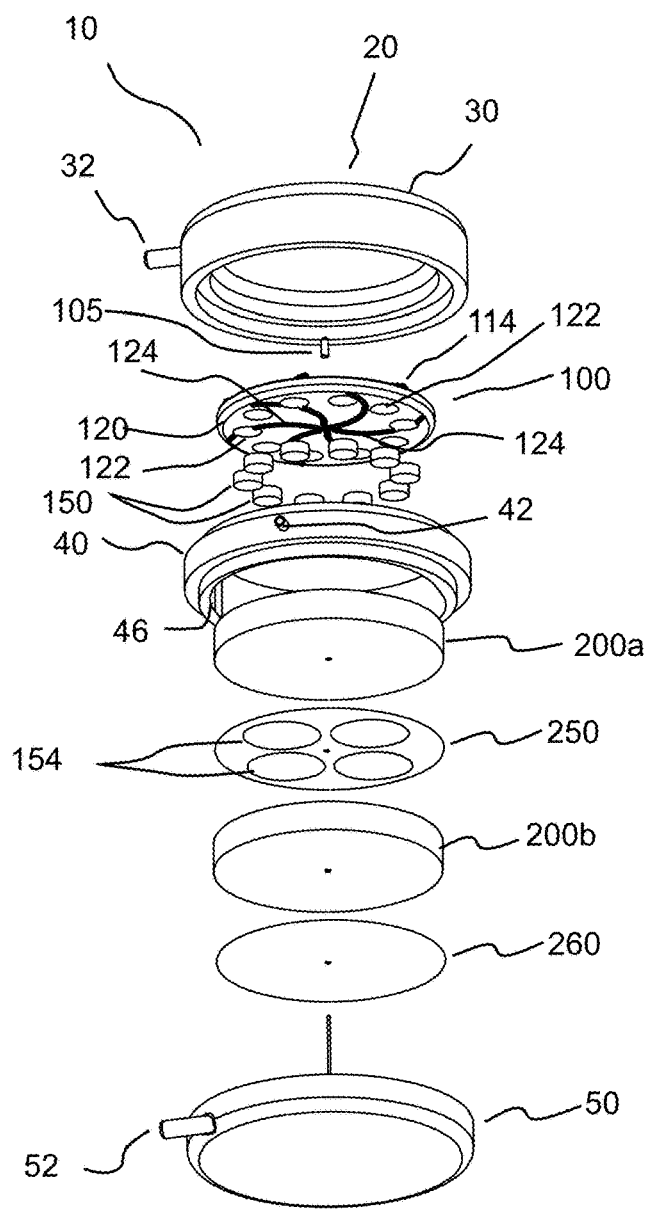
FIG. 3D illustrates a perspective, exploded view of a system hereof including a plurality of fiber bundles with a rotating or spinning element positioned therebetween.
Figure 3H:
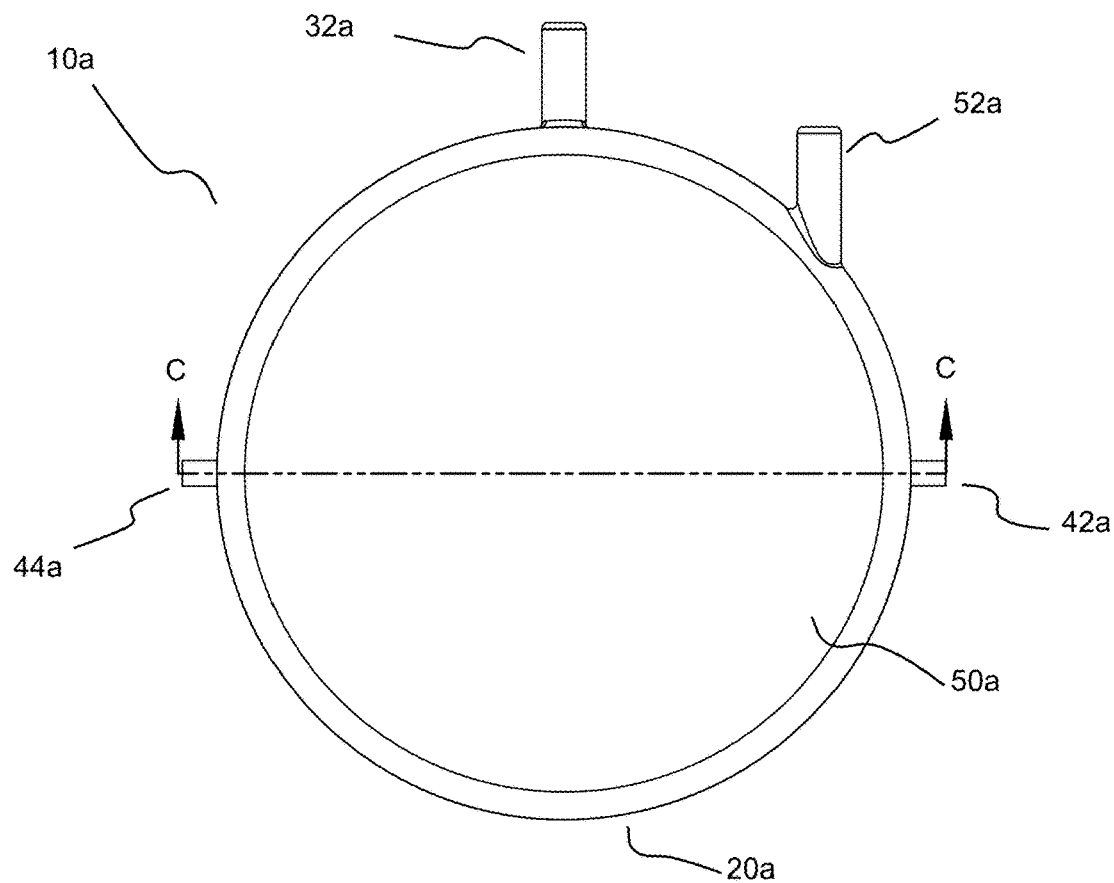
FIG. 3H illustrates a top plan view of the system of FIG. 3E.
Figure 3I:
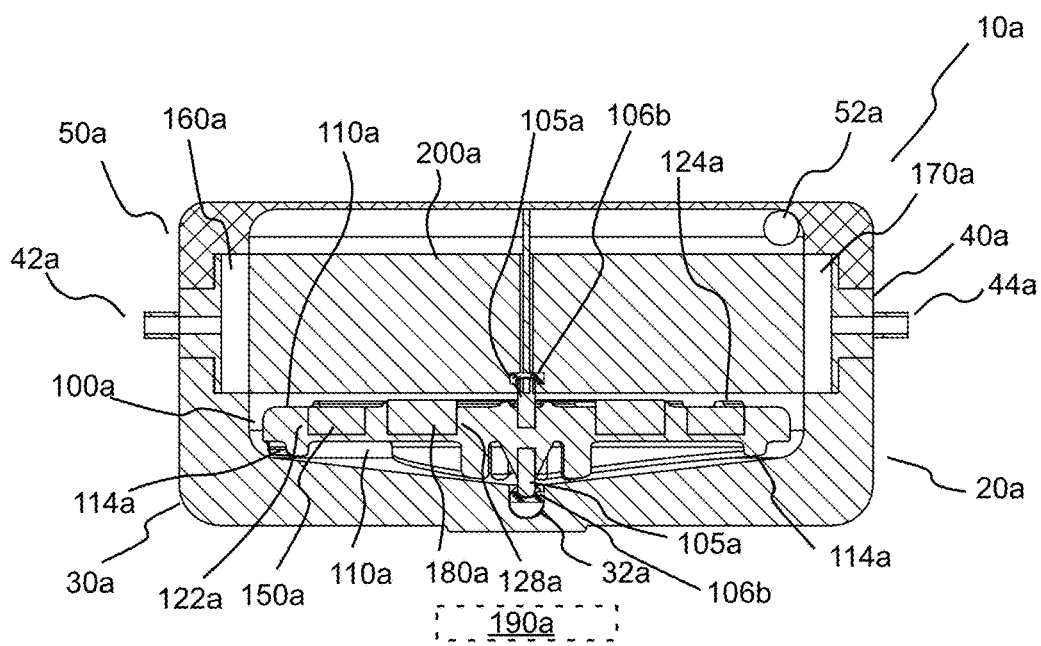
FIG. 3I illustrates a cross-sectional view of the system of FIG. 3E along section C-C of FIG. 3E.
Figure 7:
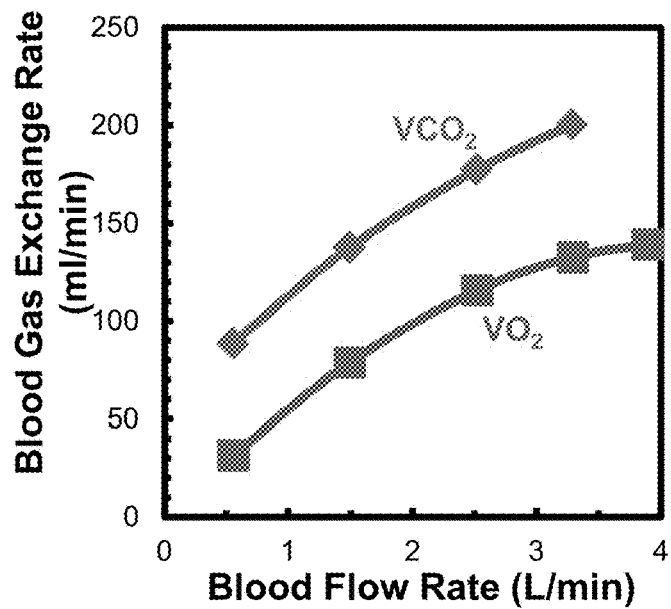
FIG. 7 illustrates the results of a study of blood gas exchange rate as a function of blood flow rate.

The $O_2$ and $CO_2$ exchange rates were also measured as a function of flow rate for system 10 using well established in-vitro protocols, and results are illustrated in FIG. 7. In a representative operating range of interest of, for example, 2-3.5 LPM, $CO_2$ removal was significant (that is, from 150 ml/min to over 200 ml/min, which is very close to the full metabolic requirements for $CO_2$ elimination). In practice, the $CO_2$ removal rate can be adjusted downward by either reducing sweep gas flow through system 10 or by adding some $CO_2$ to the $O_2$ sweep gas. In the flowrate range described above, the $O_2$ exchange varied from 80 to 140 ml/min, which may be increased via optimization. For example, CFD analysis indicates that certain design changes may boost $O_2$ exchange. For example, one may optimize active mixing within system 10 by, for example, making impeller shape changes or by adding an additional rotating surface. A second impeller or moving/rotating/spinning element or surface may, for example, be added at the bottom of fiber bundle 200 to increase gas exchange efficiency. In other embodiments (as illustrated, for example, in FIG. 3D), a plurality of fiber bundles may be used with impellers or moving/rotating/spinning surface at the ends of the plurality of fiber bundles and between the individual fiber bundles. In the embodiment of FIG. 3D, system 10 includes a first fiber bundle 200a and a second fiber bundle 200b. A rotating element 250 in the form of a disk may, for example, be placed between fiber bundle 200a and second fiber bundle 200b. Another rotating element 260 may, for example, be placed adjacent (below in the illustrated orientation) second fiber bundle 200b. Intermediate rotating element 250 may, for example, include holes or passages 154 therethrough which may be relatively large to, for example, allow net blood flow from one bundle into the next fiber bundle, while still imparting further velocity fields via the rotation of element 250. Second rotating element 260 may likewise include holes or passages. Either or both of first rotating element 250 and second rotating element 260 may, for example, be provided with vanes or other extending axially extending elements to enhance velocity fields created thereby. Additional fiber bundles and rotating element may be provided in a generally serial arrangement along the axis of the system. One may improve the flow distribution into the fiber bundle(s) by, for example, optimizing the second stage of the two-stage impeller pump 100 of system 10 and/or other moving/rotating elements thereof.

In a number of embodiments, passages or holes may be formed through the impeller or other rotating element that is used to create a pressure differential (for example, impeller 100 or impeller 100a). Although such holes or passages create inefficiency in pumping by creating leakage, the associated leakage recirculation may decrease the risk of clotting and increase active mixing. The pressure loss associated with recirculation leakage may be offset by increasing the rate of spin of the impeller, which will enhance recirculation and active mixing. Such systems may be readily optimized to, for example, maximize active mixing/efficiency and/or minimize the likelihood of blood trauma/clotting.

Figure 8:
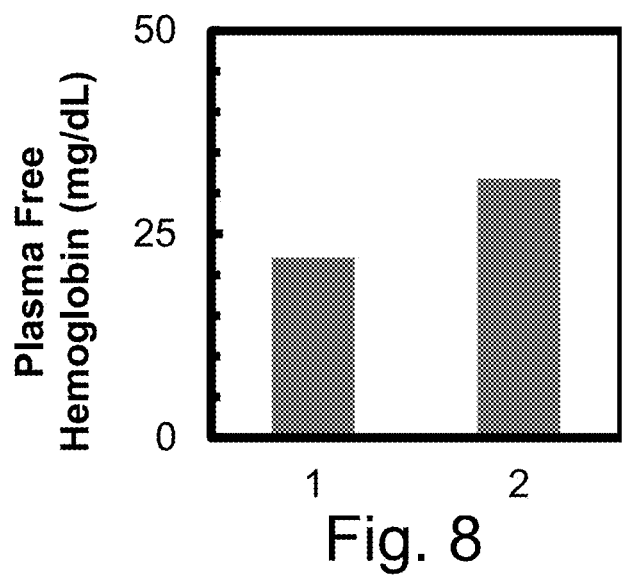
FIG. 8 illustrates the results of a study of plasma free hemoglobin.

In the in-vitro gas exchange tests, hemolysis data was obtained by measuring plasma free hemoglobin (pfHb) before (labeled 1) and after (labeled 2) the 8 hour gas exchange test as illustrated in FIG. 8. While the increase in pfHb was modest. The tests underlying the data of FIG. 8 were run over a range of flowrates and operating speeds with some short periods of low flow while inlet blood gas conditions were being adjusted.

In some embodiments, zwitterionic-based hemocompatible coatings may replace the heparin coating currently used on siloxane plasma resistant hollow fiber membranes. Hemocompatible coating development may, for example, be guided by gas permeance measurements on coated fibers and in-vitro comparative hemocompatibility tests.

As described above, computational fluid dynamics (CFD) may be used to optimize the design and operational parameters of system 10 to meet requirements for blood pumping, gas exchange, priming volume, and form factor. CFD may be used to simulate blood flow and gas exchange. Upon validation, CFD may be incorporated into design optimization algorithms.

In that regard, CFD is an effective tool to streamline the design process of, for example, blood pumps and oxygenators. Developed and validated CFD simulations may be combined with formal design optimization to analyze and refine the design of system 10 and blood contacting components thereof (including, for example, the impeller region, other rotational surfaces, the fiber bundle, and connecting conduits). Optimization objectives may, for example, include maximizing gas exchange and minimizing the size of system 10. The objectives may have constraints imposed to ensure sufficient pumping capacity, while minimizing trauma to blood. Optimization provides an optimal set of design features such as impeller size and configuration, fiber bundle layout, active mixing surfaces and blood inlet and outlet ports.

CFD simulation may, for example, include a number of approaches. The laminar Navier-Stokes equations may, for example, be solved using commercial codes such as Fluent (v14, ANSYS Inc., Canonsburg, Pa.) and Loci-Stream (v1.6.1, Streamline Numerics, Gainesville, Fla.). Turbulence modeling in the rotor cavity region of the device may be applied as needed in regions of sufficient Reynolds number or in the event of a disparity between CFD predictions and flow visualization results. The fiber bundle may be modeled as a single lumped continuum (porous medium) using a modified Ergun equation to characterize the pressure losses and superficial velocity field therein. Oxygen and carbon dioxide exchange may, for example, be modeled using a convection-diffusion-source mass transfer approach of along with a nonlinear $O_2$ gas transfer model and a nonlinear $CO_2$ model. We developed a CFD model of complex blood flow and gas exchange in hollow fiber bundles which was experimentally validated. The CFD model is suitable to predict subtle features of impeller-generated flow patterns and the overall gas exchange.

Figure 9:
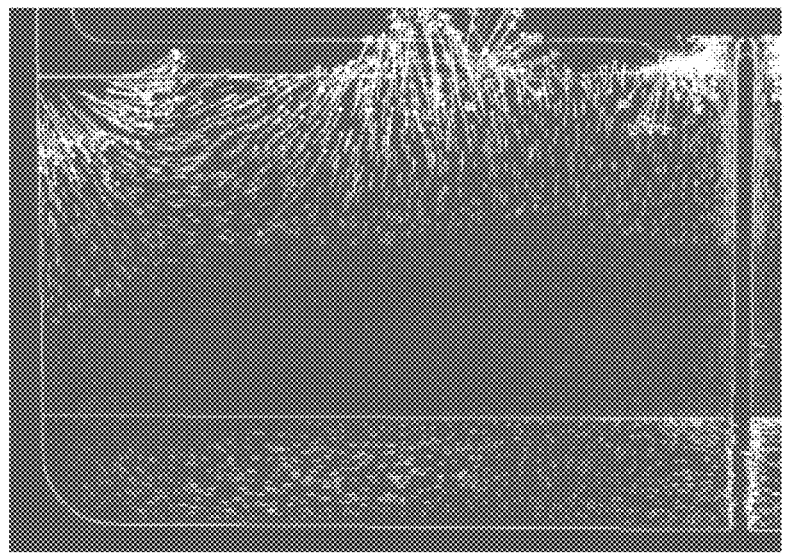
FIG. 9 illustrates a simulated velocity field which shows the direct penetration of disturbed flow from the impeller into the fiber bundle of the system of FIG. 1A
Figure 10:
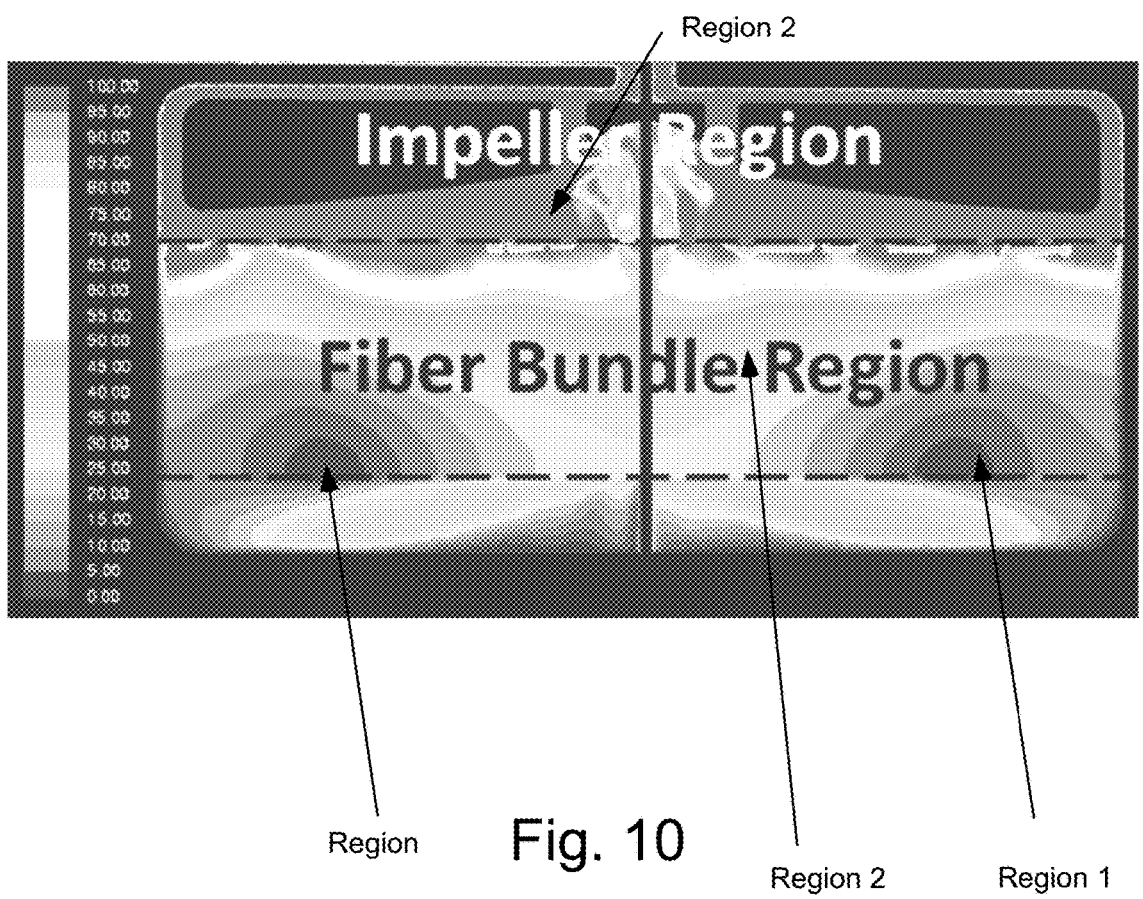
FIG. 10 illustrates a comparison of simulated velocity fields with and without impeller rotation, showing that the disturbed flow resulting from impeller rotation propagates about ⅓ or ½ the distance into the fiber bundle, which is demarcated between the dashed lines of FIG. 10.

Preliminary CFD analysis of blood flow has been performed for system 10, and the CFD predictions were generally consistent with experimental data. The impeller design produces sufficient pressure head to pump fluid through the fiber bundle with excess pressure to provide blood pumping capacity. A simulated velocity field illustrated in FIG. 9 clearly shows the direct penetration of disturbed flow from impeller 100 into the fiber bundle. This direct interaction of the impeller field with the fiber bundle produces active mixing as discussed above, which enhances gas exchange. A "disturbed" flow index (DFI) (defined as the fractional increase in the magnitude of velocity compared to that which would occur by passive flow at the same flowrate through system 10 without impeller rotation) was computed. In FIG. 10, regions 1 or blue regions (DFI=1) indicate little disturbance proceeding to a regions 2 or green regions (DFI=50) and regions 3 or red regions (DFI=100). In the embodiment studied, the disturbed flow propagates about ⅓ or ½ the distance into fiber bundle 100, which is demarcated between the dashed lines of FIG. 10. The fiber bundle in the studied embodiments was approximately is 0.88 inches in depth (0.0224 meter) and include 62 layers of fiber fabric as described above. The disturbed flow (active mixing) the propagated approximately, 0.29 to 0.44 inches (or approximately 0.0074 to 0.0112 meters). The studied embodiments were not, however, optimized for depth of active mixing. FIG. 10 suggests, for example, that a rotating secondary impeller or surface below fiber bundle 200 may further disturb the flow field within the bundle.

One may computationally also assess the hemocompatibility of system 10 using blood damage models for hemolysis, platelet activation, and thrombogenicity. A number of such models have been developed specifically for implementation with CFD.

As described above, a formal gradient-based design optimization may be applied to system 10. Such a formal approach differs from most so-called CFD "design optimization" procedures found in the literature, which are simply numerical variations of "trial and error." Design features such as rotor blade profile, blade angles, and fiber bundle dimensions can be mathematically parameterized and modified automatically by a numerical gradient-based optimization scheme to maximize gas exchange efficiency while simultaneously enhancing hemocompatibility as defined by numerical blood damage metrics. Discrete sensitivity analysis in the Loci-Stream CFD software may be implemented to provide highly-accurate sensitivity gradients of the objective function and constraints with respect to the design parameters. The NASA-funded Discrete software (Optimal LLC, Starkville, Miss.) may, for example, be used to effect shape changes to system 10.

Because of rather complex and coupled blood and gas flow paths, repeated numerical analyses of the complete unit can be prohibitive. Therefore, CFD optimization may be complemented with bench testing to (a) calibrate and validate the numerical analysis, and (b) evaluate the performance over the complete range of operating conditions. Direct experimental studies, although more expensive than CFD analysis, more readily provide assessment of gas exchange and surface washing as it relates to thrombogenicity. Furthermore, bench testing may reduce the need for animal studies in the design iteration process. Bench tests may, for example, be performed using well-established standards to characterize pumping ability, gas exchange, potential for hemolysis, and thrombosis. Flow visualization studies may, for example, be used to confirm that the CFD analysis predicts important features of the flow at the inlet, in the impeller region, and the outlet that may influence blood damage (shear "hot" spots) or propensity for thrombosis (stagnant loci).

To evaluate the pumping ability of system 10, one may generate pressure-flow curves over a range of possible rotation rates in a recirculating loop containing only a reservoir and system 10. Pressure head for system 10 may, for example, be measured using a differential transducer (Omega Engineering Inc., Stamford, Conn.) across the inlet and outlet. A Hoffman clamp downstream from system 10 may, for example, be used to vary the flowrate and outlet pressure at specific rotation rates. Such experiments may, for example, be conducted using a blood analogue fluid (carboxymethylcellulose in water) with a viscosity matching the asymptotic viscosity of normal blood (3.5 cP).

As describe above, zwitterionic molecular coatings may be used to improve hemocompatibility of system 10. For example, hemocompatible zwitterionic phosphorylcholine (PC) or sulfobetaine (SB) molecules may be bonded in place of heparin. A primary barrier to long-term respiratory support with artificial lungs is the hemocompatibility issue associated with the large membrane surface in contact with blood and the concomitant need for systemic anticoagulation, which can lead to bleeding complications. Zwitterionic phosphorylcholine (PC) or sulfobetaine (SB) groups provide bioinert properties that reduce protein adsorption and denaturation and have shown promising anti-thrombogenicity and anti-fouling properties on other cardiovascular devices and biosensors.

Zwitterionic based coatings (PC and SB) may, for example, be applied to aminated siloxane hollow fiber membranes for use in system 10. Gas permeance measurements on fibers modified with zwitterionic based coatings may be used to ensure that fiber permeance to $O_2$ and $CO_2$ remain sufficiently high to have a negligible impact on gas exchange performance. In-vitro hemocompatibility assays may be performed on candidate PC and SB coatings, along with the current siloxane-heparin coated fiber as a comparative control.

The base fiber membrane may, for example, be an aminated siloxane coated hollow fiber membrane in fabric form obtained from Alung Technologies. This fiber fabric is the same fiber fabric used to create the heparin coated fiber discussed above, but is used prior to heparinization process. Carboxyl end-group functional PC or SB macromolecules (short to long chain of PC or SB groups) may be prepared via a thiol-ene radical polymerization technique. The thiol-ene radical polymerization technique offers a powerful method to prepare the functional macromolecules in a simple process. The chain length of PC or SB moieties of the macromolecules can be manipulated by altering the initial monomer feeding ratio and the preparation conditions. Using the generated macromolecules for surface modification is attractive from a cost perspective and avoids concerns with the release of adsorbed high molecular weight PC or SB bearing polymers.

The carboxyl end-group functionalized PC or SB macromolecules may, for example, be covalently immobilized on the aminated hollow fiber surfaces by a condensation reaction between the carboxyl groups and surface amino groups. This may, for example, be done by placing the fiber fabric within tubes with the synthesized mPC-COOH or mSB-COOH aqueous solution, adding condensation catalyst, 1-ethyl 3-(3-dimethylaminopropyl) carbodiimide hydrochloride (EDC) and N-hydroxysuccinimidyl (NHS), and continuously mixing at 37° C. for 24 hrs to allow amide bond formation between the amino groups and carboxyl groups. The modification density and effectiveness may be assessed depending on the functional macromolecules, chain length of the molecules and the reactivity (density) of the amino groups on the aminated hollow fibers. The surface composition and the grafting density on the modified hollow fiber may be analyzed by X-ray photoelectron spectroscopy (XPS).

Figure 11:
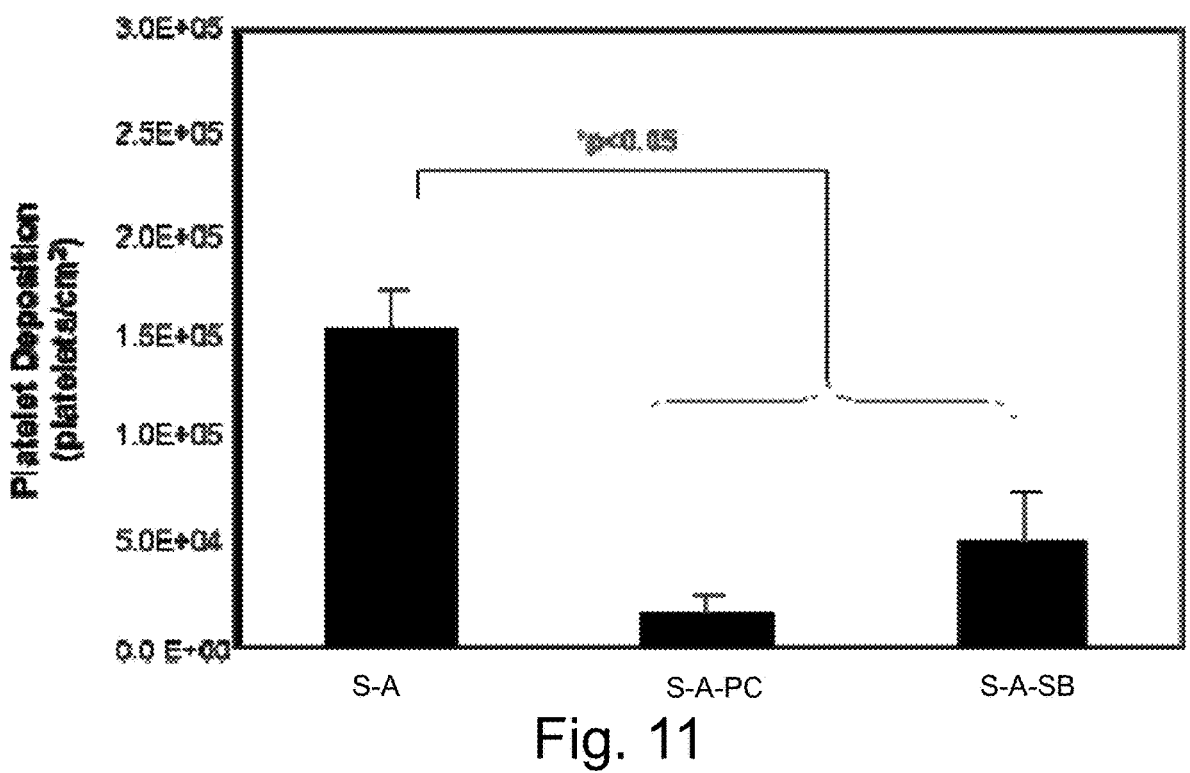
FIG. 11 illustrates the results of platelet deposition studies of aminated siloxane fiber (S-A) modified with zwitterionic phosphorylcholine (S-A-PC) and or zwitterionic sulfobetaine (S-A-SB) macromolecules.

We have demonstrated that we can successfully modify the aminated siloxane fiber (S-A) with PC (S-A-PC) and SB (S-A-SB) macromolecules, and that the modified fibers showed significantly reduced platelet deposition compared to the uncoated control fiber (see FIG. 11).

The modification density varies depending on the functional macromolecular chain length and the reactivity (density) of amino groups on the aminated hollow fibers. Further amination treatments using radio frequency glow discharge (RFGD) may be used to introduce further reactive amino groups on the hollow fibers. Conventional free radical polymerization as well as controlled/living radical polymerization such as reversible fragmentation chain-transfer (RAFT) polymerization or atom-transfer radical polymerization (ATRP) may be used. The modification techniques may be varied depending on the surfaces and the demands of the modification efficiency. For example, conventional free radical polymerization may be better for simple preparation and modification of high molecular weight of PC or SB based polymers, and other controlled/living radical polymerization techniques may be better for the preparation of controlled carboxyl functional polymers or generation of controlled polymer brush layer on the hollow fiber surfaces. Further surface modification techniques may be used. Cellular (endothelial) coatings have, for example, also shown promise.

In measuring gas permeance of modified fibers, coated fibers may be mounted in a gas-gas permeance module (one fiber/module) with one end occluded and the other connected (epoxied) to a gas flow pathway. In a number of studies, a total of six modules are, for example, prepared and tested for type coated fiber. $CO_2$ or $O_2$ is introduced into each module via an applied pressure and the rate of gas diffusion through the fiber wall may be measured using a bubble flow meter connected to the outlet gas pathways from all modules. Permeance (in) may be calculated by the rate of gas flow divided by differential pressure and the exposed fiber surface area to gas. Permeance measurements may be made at both 23° C. and 37° C. As the coatings are molecular based, it is not expected that gas permeance of coated fibers will be reduced compared to the siloxane-heparin control. For application in system 10, $CO_2$ and $O_2$ permeances above $1\times10$-4 and $1\times10$-5 ml/s/cm2/cmHg, respectively, will be targeted to ensure minimal effects of the coatings on gas. Siloxane-heparin fibers meets those targets.

In bench studies of platelet adhesion, platelet activation and thrombus formation, whole ovine blood may, for example, be collected by jugular venipuncture. Hollow fiber samples with equivalent surface areas may be placed in Vacutainer® tubes filled with the heparinized blood and incubated at 37° C. on a hematology mixer. After contact with the ovine blood, the surfaces may be rinsed and fixed in glutaraldehyde and prepared for scanning electron microscopy (SEM) to observe the platelet adhesion and the morphologies. The number of platelets deposited on hollow fiber samples may be determined by a lactate dehydrogenase (LDH) assay. The percentage of activated platelets in the bulk phase of the blood contacting the hollow fiber samples may be quantified with flow cytometric assay using annexin V protein or an antihuman CD62P antibody.

In-vivo animal studies may also be used to study the performance of system 10 when connected to a circulatory system similar to humans and to establish correlations between functional performance in bench testing and animal testing. These studies may be used for delineating the physiological and hemocompatibility impact of system 10 in a mammalian model. Studies may, for example, be performed in healthy sheep, as is standard practice in device development programs for blood pumps and artificial lungs.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A extracorporeal system for lung assist comprising:
a housing,
a blood flow inlet in fluid connection with the housing;
a blood flow outlet in fluid connection with the housing;
a generally cylindrical fiber bundle comprising a plurality of hollow gas permeable fibers adapted to permit diffusion of gas between blood and an interior of the hollow gas permeable fibers, the generally cylindrical fiber bundle being positioned between the blood flow inlet and the blood flow outlet such that blood flows around the plurality of hollow gas permeable fibers when flowing from the blood flow inlet to the blood flow outlet, the plurality of hollow gas permeable fibers extending generally perpendicular to the direction of bulk flow of blood through the housing;
a gas inlet in fluid connection with the housing and in fluid connection with inlets of the plurality of hollow gas permeable fibers;
a gas outlet in fluid connection with the housing and in fluid connection with outlets of the plurality of hollow gas permeable fibers; and
at least one moveable element positioned external to the generally cylindrical fiber bundle which is axially spaced from and directly adjacent a surface of the generally cylindrical fiber bundle via which blood enters the generally cylindrical fiber bundle, movement of the at least one moveable element creating velocity fields in blood flow contacting the plurality of hollow gas permeable fibers.

2. The system of claim 1 wherein the system is a paracorporeal system.

3. The system of claim 2 wherein the plurality of hollow gas permeable fibers comprise a plurality of layers of fiber fabric, each of the plurality of layers of fiber fabric comprising hollow gas permeable fibers, wherein adjacent layers of fiber fabric are rotated relative to each other such that the orientation of the plurality of hollow gas permeable fibers in adjacent layers of fiber fabric are of a different orientation.

4. The system of claim 2 wherein the plurality of hollow gas permeable fibers comprise at least one zwitterionic species tethered on surfaces thereof.

5. The system of claim 2 wherein the system is adapted to adjustably deliver flows in the range of approximately 2 to 4 liters per minute.

6. The system claim 2 further comprising a first pivot bearing on a first side of the at least one moveable element and a second pivot bearing on a second side of the at least one moveable element.

7. The system of claim 2 wherein the at least one moving moveable element comprises a rotating impeller adapted to pump blood from the blood flow inlet to the blood flow outlet, the rotating impeller rotating in a plane generally parallel to an orientation of the plurality of hollow gas permeable fibers.

8. The system of claim 7 wherein a surface of the rotating impeller is directly adjacent the plurality of hollow gas permeable fibers and rotation thereof causes active mixing within the plurality of hollow gas permeable fibers.

9. The system of claim 7 wherein the impeller comprises a disk, a first plurality of vanes on a first side of the disk and a second set of vanes on a second side of the disk.

10. The system of claim 7 further comprising a rotating element positioned within the housing adjacent to the plurality of hollow gas permeable fibers on an opposite side thereof of the rotating impeller.

11. The system of claim 10 wherein the rotating element is a second impeller.

12. The system of claim 7 including a system to offset hydrodynamic force.

13. The system of claim 12 wherein the system to offset hydrodynamic force comprises a first magnet in operative connection with the rotating impeller which cooperates with a second magnet to create a repellant force therebetween.

14. The system of claim 1 wherein blood is blocked from flowing to the gas inlet and the gas outlet.

15. The system of claim 1 wherein the generally cylindrical fiber bundle is formed from a plurality of layers of fiber fabric, each of the plurality of layers of fiber fabric comprising hollow gas permeable fibers, wherein adjacent layers of fiber fabric are rotated relative to each other such that the orientation of the plurality of hollow gas permeable fibers in adjacent layers of fiber fabric are of a different orientation.

16. The system of claim 15 wherein a first seal is formed between the generally cylindrical fiber bundle and the housing at a first position and a second seal is formed between the generally cylindrical fiber bundle and the housing at a second position, rotated around the circumference of the generally cylindrical fiber bundle from the first position, to form a gas inlet manifold in fluid connection with the gas inlet on a first side of the first seal and the second seal and a gas outlet manifold in fluid connection with the gas outlet on a second side of the first seal and the second seal, the first seal and the second seal blocking fluid connection between the gas inlet manifold and the gas outlet manifold.

17. A method for extracorporeal lung assist comprising:
providing a generally cylindrical fiber bundle comprising a plurality of hollow gas permeable fibers within a housing, the plurality of hollow gas permeable fibers being adapted to permit diffusion of gas between blood and an interior of the hollow gas permeable fibers, the generally cylindrical fiber bundle being positioned between a blood flow inlet and a blood flow outlet such that blood flows around the plurality of hollow gas permeable fibers when flowing from the blood flow inlet to the blood flow outlet, the plurality of hollow gas permeable fibers extending generally perpendicular to the direction of bulk flow of blood through the housing;
flowing a sweep gas including oxygen through the plurality of hollow gas permeable fibers; and
moving at least one moveable element positioned external to the generally cylindrical fiber bundle which is axially spaced from and directly adjacent a surface of the generally cylindrical fiber bundle via which blood enters the generally cylindrical fiber bundle, movement of the at least one moveable element creating velocity fields in blood flow contacting the plurality of hollow gas permeable fibers.

18. The method of claim 17 wherein paracorporeal lung assist is provided.

19. A extracorporeal system for lung assist comprising:
a housing,
a blood flow inlet in fluid connection with the housing;
a blood flow outlet in fluid connection with the housing;
a generally cylindrical fiber bundle comprising a plurality of hollow gas permeable fibers adapted to permit diffusion of gas between blood and an interior of the hollow gas permeable fibers, the generally cylindrical fiber bundle being positioned between the blood flow inlet and the blood flow outlet such that blood flows around the plurality of hollow gas permeable fibers when flowing from the blood flow inlet to the blood flow outlet;
a gas inlet in fluid connection with the housing and in fluid connection with inlets of the plurality of hollow gas permeable fibers;
a gas outlet in fluid connection with the housing and in fluid connection with outlets of the plurality of hollow gas permeable fibers;
at least one moveable element positioned external to the generally cylindrical fiber bundle which is axially spaced from and directly adjacent a surface of the generally cylindrical fiber bundle via which blood enters the generally cylindrical fiber bundle, movement of the at least one moveable element creating velocity fields in blood flow contacting the plurality of hollow gas permeable fibers;
a first pivot bearing on a first side of the at least one moveable element; and
a second pivot bearing on a second side of the at least one moveable element.

20. The system of claim 19 wherein blood entering the housing flows across the first pivot bearing and the second pivot bearing to flush a surface of the first pivot bearing and a surface of the second pivot bearing.

* * * * *